(12) United States Patent
Benner et al.

(10) Patent No.: US 8,034,923 B1
(45) Date of Patent: Oct. 11, 2011

(54) REAGENTS FOR REVERSIBLY TERMINATING PRIMER EXTENSION

(76) Inventors: Steven Albert Benner, Gainesville, FL (US); Daniel Hutter, Gainesville, FL (US); Nicole Aurora Leal, Gainesville, FL (US); Fei Chen, Gainesville, FL (US)

( * ) Notice: Subject to any disclaimer, the term of this patent is extended or adjusted under 35 U.S.C. 154(b) by 410 days.

(21) Appl. No.: 12/383,776

(22) Filed: Mar. 27, 2009

(51) Int. Cl.
*C07H 21/02* (2006.01)
*C07H 21/04* (2006.01)
*C07H 19/04* (2006.01)
*C07H 19/048* (2006.01)
*C07H 19/067* (2006.01)
*C07H 19/073* (2006.01)
*C07H 19/167* (2006.01)
*C07H 19/173* (2006.01)

(52) U.S. Cl. .................. 536/25.1; 536/25.3; 536/25.31; 536/25.6; 536/26.1; 536/26.2; 536/26.26

(58) Field of Classification Search ......................... None
See application file for complete search history.

(56) References Cited

U.S. PATENT DOCUMENTS

| 6,214,551 B1 * | 4/2001 | Sanghvi et al. ................... 435/6 |
| 6,576,752 B1 * | 6/2003 | Manoharan et al. ......... 536/23.2 |
| 7,173,125 B2 * | 2/2007 | Schwartz et al. .......... 536/26.26 |

OTHER PUBLICATIONS

Trevisiol et al., "Synthesis of Nucleoside Triphosphates that Contain an Aminooxy Function for 'Post-Amplification Labelling'" European Journal of Organic Chemistry (2000) pp. 211-217.*

* cited by examiner

*Primary Examiner* — Eric S Olson

(57) ABSTRACT

Processes are disclosed that use 3'-reversibly terminated nucleoside triphosphates to analyze DNA for purposes other than sequencing using cyclic reversible termination. These processes are based on the unexpected ability of terminal transferase to accept these triphosphates as substrates, the unexpected ability of polymerases to add reversibly and irreversibly terminated triphosphates in competition with each other, the development of cleavage conditions to remove the terminating group rapidly, in high yield, and without substantial damage to the terminated oligonucleotide product, and the ability of reversibly terminated primer extension products to capture groups. The presently preferred embodiments of the disclosed processes use a triphosphate having its 3'-OH group blocked as a 3'-$ONH_2$ group, which can be removed in buffered $NaNO_2$ and use variants of Taq DNA polymerase, including one that has a replacement (L616A).

13 Claims, 15 Drawing Sheets

SEQUENCE LISTING

```
<160> NUMBER OF SEQ ID NOS: 12

<210> SEQ ID NO 1
<211> LENGTH: 24
<212> TYPE: DNA
<213> ORGANISM: Artificial Sequence
<220> FEATURE:
<223> OTHER INFORMATION: Synthetic

<400> SEQUENCE: 1
gcgtaatacg actcactatg gacg                                         24

<210> SEQ ID NO 2
<211> LENGTH: 36
<212> TYPE: DNA
<213> ORGANISM: Artificial Sequence
<220> FEATURE:
<223> OTHER INFORMATION: Synthetic
```

-continued

<400> SEQUENCE: 2
gtcttcgtgt aacgtccata gtgagtcgta ttacgc        36

<210> SEQ ID NO 3
<211> LENGTH: 36
<212> TYPE: DNA
<213> ORGANISM: Artificial Sequence
<220> FEATURE:
<223> OTHER INFORMATION: Synthetic

<400> SEQUENCE: 3
gtcttcgtgt aacgtccata gtgagtcgta ttacgc        36

<210> SEQ ID NO 4
<211> LENGTH: 36
<212> TYPE: DNA
<213> ORGANISM: Artificial Sequence
<220> FEATURE:
<223> OTHER INFORMATION: Synthetic

<400> SEQUENCE: 4
gtcttcgtgt ggcgtccata gtgagtcgta ttacgc        36

<210> SEQ ID NO 5
<211> LENGTH: 36
<212> TYPE: DNA
<213> ORGANISM: Artificial Sequence
<220> FEATURE:
<223> OTHER INFORMATION: Synthetic

<400> SEQUENCE: 5
gtcttcgtgt ttcgtccata gtgagtcgta ttacgc        36

<210> SEQ ID NO 6
<211> LENGTH: 36
<212> TYPE: DNA
<213> ORGANISM: Artificial Sequence
<220> FEATURE:
<223> OTHER INFORMATION: Synthetic

<400> SEQUENCE: 6
gtcttcgtgt cccgtccata gtgagtcgta ttacgc        36

<210> SEQ ID NO 7
<211> LENGTH: 36
<212> TYPE: DNA
<213> ORGANISM: Artificial Sequence
<220> FEATURE:
<223> OTHER INFORMATION: Synthetic

<400> SEQUENCE: 7
gtcttcgtgt agcgtccata gtgagtcgta ttacgc        36

<210> SEQ ID NO 8
<211> LENGTH: 36
<212> TYPE: DNA
<213> ORGANISM: Artificial Sequence
<220> FEATURE:
<223> OTHER INFORMATION: Synthetic

<400> SEQUENCE: 8
gtcttcgtgt atcgtccata gtgagtcgta ttacgc        36

<210> SEQ ID NO 9
<211> LENGTH: 36

```
<212> TYPE: DNA
<213> ORGANISM: Artificial Sequence
<220> FEATURE:
<223> OTHER INFORMATION: Synthetic

<400> SEQUENCE: 9
gtcttcgtgt atcgtccata gtgagtcgta ttacgc                            36

<210> SEQ ID NO 10
<211> LENGTH: 9
<212> TYPE: DNA
<213> ORGANISM: Artificial Sequence
<220> FEATURE:
<223> OTHER INFORMATION: Synthetic

<400> SEQUENCE: 10 ctatggacg                                                           9

<210> SEQ ID NO 11
<211> LENGTH: 16
<212> TYPE: DNA
<213> ORGANISM: Artificial Sequence
<220> FEATURE:
<223> OTHER INFORMATION: Synthetic

<400> SEQUENCE: 11
gtgataacgt ccatag                                                  16

<210> SEQ ID NO 12
<211> LENGTH: 10
<212> TYPE: DNA
<213> ORGANISM: Artificial Sequence
<220> FEATURE:
<223> OTHER INFORMATION: Synthetic

<400> SEQUENCE: 12
ctatggacgt                                                         10
```

US 8,034,923 B1

REAGENTS FOR REVERSIBLY TERMINATING PRIMER EXTENSION

This application claims in part priority of U.S. patent application Ser. No. 11/373,415, filed Mar. 11, 2006 now U.S. Pat. No. 7,544,794.

INTRODUCTION

1. Field of the Invention

This invention relates to the field of nucleic acid chemistry, more specifically to the field of compositions and processes that can be used to analyze, modify, manipulate and capture nucleic acids. More specifically, this invention relates to processes that use compositions of matter that are nucleoside triphosphate analogs and the derived oligonucleotides, wherein the 3'-hydroxyl is blocked by a group that can be removed, and wherein these triphosphates can be accepted by enzymes that synthesize oligonucleotides from triphosphates, including terminal transferases, RNA polymerases, reverse transcriptases, and DNA polymerases.

2. Background of the Invention

A nucleoside triphosphate is said to be a terminator when a product oligonucleotide formed by its addition under enzymatic catalysis to its 3'-end cannot be further extended by the same enzyme under the same conditions. The terminator is said to be irreversible where no chemical transformation or change in conditions allows the N+1 extension product to be extendable. Under conditions where the product oligonucleotide is left substantially unharmed. For example, 2',3'-dideoxynucleoside triphosphates are irreversible terminators of primer extension. Once they are added to the 3'-end of an oligonucleotide, that oligonucleotide cannot be further extended, as it lacks the nucleophilic 3'-OH that is required for further extension. Further, no chemical reactions can convert a 2',3'-dideoxyterminated oligonucleotide into one that is terminated by a 2'-deoxyribonucleotide without substantially damaging the oligonucleotide.

Reversibly terminating triphosphates can have a substituent that is accepted by a polymerase as a triphosphate but not at the 3'-end of a primer, where that substituent can be removed. Sometimes, the substituent can be appended to the nucleobases, as in reversible terminators described by Metzker. Other times, the substituent is attached to the 3'-OH group itself, where it blocks primer extension until it is removed to regenerate a free 3'-OH group.

U.S. patent Ser. No. 11/373,415 disclosed the 3'-ONH$_2$ substituent as a reversible terminator. It discussed this substituent in the context of architectures for "sequencing-by-synthesis", and more specifically sequencing of the type known as "sequencing using cycle reversible termination" (SuCRT). This is a strategy that extends a primer by template-directed addition of one nucleotide at a time, where the nucleotide added has a discernable tag (for example, a fluorescent group of a certain color). Because of the terminator properties of the nucleoside triphosphate, primer extension is stopped for a time after each nucleotide incorporated. In that time, the extended primer is examined to determine what nucleotide is incorporated, and to infer the nucleotide in the template that directed the incorporation.

When the output is fluorescence, this implementation of the strategy requires:

(a) Four analogues of dATP, dTTP, dGTP, and dCTP, each carrying a fluorescent dye with a different color, with the 3'-end blocked so that immediate elongation is not possible.

(b) The four analogues must be incorporated to allow the elongation reaction to be completed before undesired reactions occur and avoid ragged ends from incomplete incorporation.

(c) The incorporation must be substantially faithful. Mismatched incorporation, if not corrected by proofreading, will lead to the loss of strands if the polymerase does not extend efficiently a terminal mismatch. This will gradually erode the intensity of the signal, and may generate "out of phase" signals that confuse the reading of the output downstream.

(d) The dye and the group blocking the 3'-OH group must be cleaved with high yield to allow the incorporation of the next nucleotide to proceed. Incomplete cleavage will erode the intensity of the signal or generate "out of phase" signals that confuse downstream reading. For single molecule sequencing, failure to cleave the 3'-OH blocking group may lose a cycle of sequence data collection.

(e) The growing strand of DNA should survive the washing, detecting and cleaving processes.

While reannealing is possible, conditions that allow the DNA primer and template to remain annealed are preferable.

An outline of this strategy is provided in U.S. Pat. No. 6,664,079,

Neither disclosed nor claimed in U.S. application Ser. No. 11/373,415 is a series of processes that apply reversible terminators using enzymatic reactions based on DNA polymerases, RNA polymerases, reverse transcriptases, and terminal transferases. Because each class of enzymes has evolved for billions of years to accept nucleoside triphosphates, these are the subject of the current patent application, which is explicitly directed to inventions that are processes that are not comprised within the architecture illustrated by U.S. Pat. No. 6,664,079.

BRIEF DESCRIPTION OF THE DRAWINGS

FIG. 10 (B). Example 6. Correlation between the ability of various Taq polymerase variants of PD library to accept reversibly and irreversibly blocked thymidine triphosphates.

DETAILED DESCRIPTION OF THE INVENTION

Figure 1:
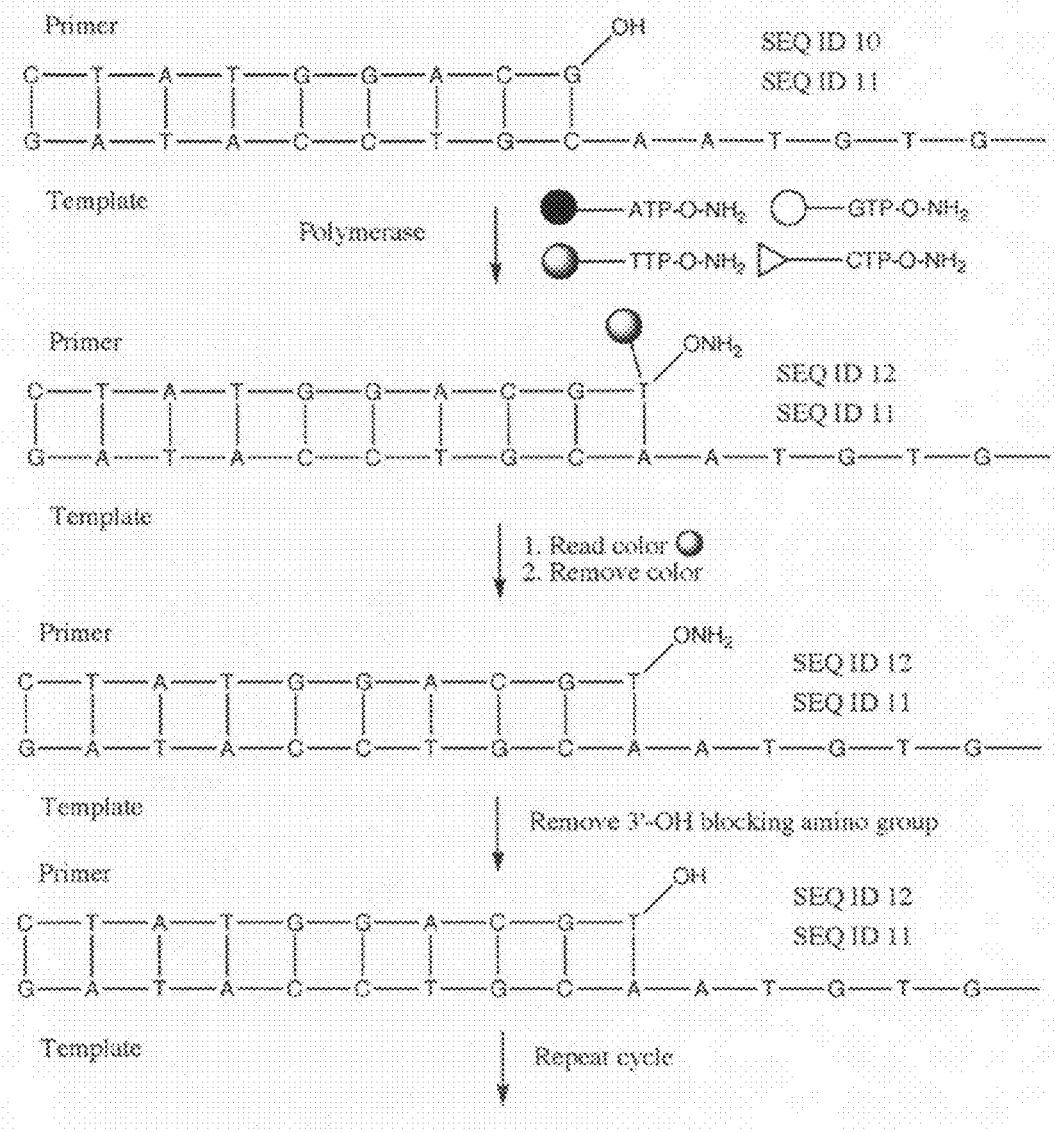
FIG. 1. Schematic for sequencing-by-synthesis using the 3'-ONH$_2$ group as a small, removable 3'-blocking group. The circles and triangles represent fluorescent groups having different colors. The 3'-blocked fluorescently tagged nucleotide is incorporated by a DNA polymerase. Chain termination then stops, because of the 3'-blocking group. The fluorescence color is read (determining which nucleotide was added), the fluorescent group is removed, and the 3'-OH is deblocked. The cycle is then be repeated. The instant invention concerns processes and compositions that are different from those shown here.

Natural enzymes have evolved for billions of years to accept their natural substrates. Accordingly, it is difficult or impossible to predict whether or not an enzyme will accept an analog of a natural substrate. In some cases, they do. In other cases, the analog of the substrate binds to the enzyme but is not transformed; substrate analogs having this behavior are very often enzyme inhibitors.

This is especially true for enzymes that handle DNA. Especially for DNA polymerases, RNA polymerases, and reverse transcriptases, enzymes have evolved not only to accept the triphosphates of A, T (or U), G and C, but also to accept them with high fidelity.

Further, enzymes have evolved in the context of a cell that contains many other compounds to avoid having naturally occurring compounds be substrates for enzymes when this is not desired. For example, the enzyme known as terminal deoxyribonucleotide transferase (also known as terminal transferase or TdT) attaches 2'-deoxyribonucleotides in an untemplated fashion to the 3'-OH group of an oligonucleotide. It does so in an intracellular environment that contains a large amount of ribonucleoside triphosphates. Therefore, perhaps naively, one might expect that TdT would inspect closely the 3'-end of an incoming substrate to make certain that the accepted nucleoside triphosphate has the proper 2'- and 3'-substituents. This, by analogy, would imply to one of ordinary skill in the art that TdT would not accept a 3% deoxyribonucleoside triphosphate having a 3'-$ONH_2$ unit, which was disclosed in U.S. Ser. No. 11/373,415, which is incorporated herein by reference.

While attempting to use TdT to remove trace amounts of 3'-deoxyribonucleoside triphosphates from 3'-deoxyribonucleoside triphosphate having a 3'-$ONH_2$ unit following this rationale, it was discovered that this was not the case. TdT was discovered to be able to accept 3'-deoxyribonucleoside triphosphate having a 3'-$ONH_2$ unit. It occurred to us following this discovery that this would have use, for example, for tagging circulating single stranded DNA in a way that, after capture, the 3'-$ONH_2$ unit could be used and the captured DNA could be cloned, further extended, or otherwise transformed. The instant application claims processes that involve these steps. One presently preferred embodiment for capture of a 3'-$ONH_2$ terminated oligonucleotide is as an oxime, formed with an aldehyde or ketone. Another presently preferred embodiment has one substituent of this oxime attached to a solid support. The 3'-$ONH_2$ unit may be regenerated from the oxime by hydrolysis, or more preferably, by treating with an amine, a hydrazine, or a hydroxylamine or alkoxyamine.

The regeneration of a 3'-$ONH_2$ unit using chemical reagents must leave the oligonucleotide substantially undamaged if it is to serve as a substrate for further enzymatic processes, including enzymatic extension in either a templated process (exploiting, for example, a DNA polymerase, a reverse transcriptase, or an RNA polymerase) or an untemplated process (exploiting, for example, a terminal transferase), or even for subsequent cloning. The extent of damage that can be tolerated depends on the specific application, as appreciated by one of ordinary skill in the art. Further, the regeneration should proceed in high yield, and preferably in a yield in excess of 90%, for the most useful applications. Absent experimentation, it is not obvious that such transformations are possible.

Accordingly, this application discloses results of experiments that allow the regeneration of a 3'-$ONH_2$ unit in an oligonucleotide without substantial degradation of the oligonucleotide and in high yield. The presently preferred process to achieve these ends uses buffered sodium nitrite and nitrous acid as a reagent to transform the 3'-$ONH_2$ unit to give a 3'-OH moiety. Data are provided that show that this process is essentially complete at room temperature in 2 minutes with less than one tenth of one percent of the nucleobases in a standard oligonucleotide being damaged under the preferred conditions. The presently preferred pH for that process is between pH 5 and pH 7 and a total nitrite concentration between 100 mM and 1 M. Processes involving this removal are also part of the instant invention.

This discovery of conditions that allowed high yielding regeneration of the 3'-$ONH_2$ unit while allowing the oligonucleotide product to be used in subsequent enzymatic transformations and processes caused us to explore polymerases that might incorporate triphosphates carrying the 3'-$ONH_2$ unit in a template directed fashion. THERMINATOR™, sold in various forms by New England Biolabs, was effective at doing so. We also screened a large number of Taq variants that were disclosed in U.S. patent application Ser. No. 12/074,039, which is incorporated herein by reference. Two variants are presently preferred. One of these contained the mutation at position 667, an amino acid whose side chain is in contact with the deoxyribose ring of the incoming triphosphate, a mutation reported in 1996 by Tabor and Richardson (note that various numbering schemes differ in the precise assignment of residue numbers to Taq polymerase; this corresponds to position 664 in the Tabor-Richardson numbering scheme). This mutation replaced a phenylalanine in contact with the 2'-deoxyribose ring by a tyrosine.

Unexpected as an outcome of this experimentation was the observation that other amino acid replacements in Taq DNA polymerase also led to variants better able to use nucleoside triphosphates carrying a 3'-$ONH_2$ unit. The presently preferred variants are PD-42 (Taq A597T, L616A, F667Y, E745H, also sometimes referred to as variant 442) and PD-58 (E520G, K540I, L616A, also sometimes referred to as variant 475). Variants containing only the L616A replacement were also discovered to be effective to use nucleoside triphosphates carrying a 3'-$ONH_2$ unit.

These studies discovered a correlation between the ability of various Taq polymerase mutants to accept 2',3'-dideoxynucleoside triphosphates, an irreversible terminator, and 2'-deoxynucleoside triphosphate carrying the 3'-$ONH_2$ unit, a reversible terminator. This prompted the invention of processes that presents these two at the same time. A teaching of the instant invention is that competition between those two substrates, one that irreversibly terminates primer extension, the other in a process that reversibly terminates primer extension, in a polymerase extension reaction, has utility in detecting single nucleotide variants, and for other applications.

Consider, for example, a process seeking to detect a single nucleotide polymorphism (SNP) at a preselected site in an oligonucleotide. Consider as an example where the site is naturally A; a SNP would therefore have a C, G, or T at that site. Consider now a process whereby a primer is presented to that oligonucleotide where the first step involves template directed extension of that primer to incorporate a nucleotide opposite the SNP site. If that process exploits the 2',3'-dideoxynucleoside triphosphate of T, and the 2'-deoxynucleoside triphosphates of C, A, and G having a removable 3'-ONH$_2$ unit, any primer encountering the natural form of the oligonucleotide will be irreversibly capped by a 2',3'-dideoxynucleotide end, while any primer that encountered a SNP form of the oligonucleotide would be reversibly capped. Removal of the 3'-ONH$_2$ unit would permit the second to be (for example) PCR amplified, cloned or sequenced, with the first irretrievably unable to be PCR amplified, cloned or sequenced. This is therefore a process that can detect or discover SNPs.

Placing irreversibly terminating and reversibly terminating triphosphates in competition has special merits. While not wishing to be bound by theory, one arises because by placing the two in competition, a polymerase is not given a choice between doing a "wrong thing" (misincorporating a mismatch) and doing nothing; when both unnatural triphosphates are present, the polymerase has the opportunity to execute a matched extension for both the natural and SNP variants. Further, once irreversibly terminated, an oligonucleotide can no longer generate an assayable product, either by PCR, sequencing or by cloning. In contrast, the product that has the 3'-ONH$_2$ unit can be captured (in the presently preferred embodiment of the instant invention, as an oxime). After it is captured, through removal of the 3'-ONH$_2$ unit, the oligonucleotide can support PCR amplification, cloning, or other detection architectures well known in the art. The discovery of a correlation between the ability of a polymerase to accept these in competition provides further enablement for such processes.

Those of ordinary skill in the art will recognize that a single oxygen atom in the triphosphate moiety can be replaced by a sulfur atom, and that a single phosphorus atom can be replaced by a radioisotopic phosphorus atom. The thiotriphosphates have applications that are well known in the art, including the ability to be captured and the ability to render an oligonucleotide resistant to exonuclease activity.

Thus, the teachings of the invention include:

(a) Processes by which TdT appends a nucleotide having a 3'-ONH$_2$ unit in a template-independent fashion.

(b) Processes by which THERMINATOR and various mutants of Taq (as well as other enzymes known in the art) append a nucleotide having a 3'-ONH$_2$ unit in a template-dependent fashion.

(c) These polymerases can incorporate in competition reversibly terminated and irreversibly terminated triphosphates.

(d) Conditions are presented wherein following removal of the 3'-blocking moiety leads to products that can support continued extension by enzymatic processes.

EXAMPLES

Example 1

Figure 2:
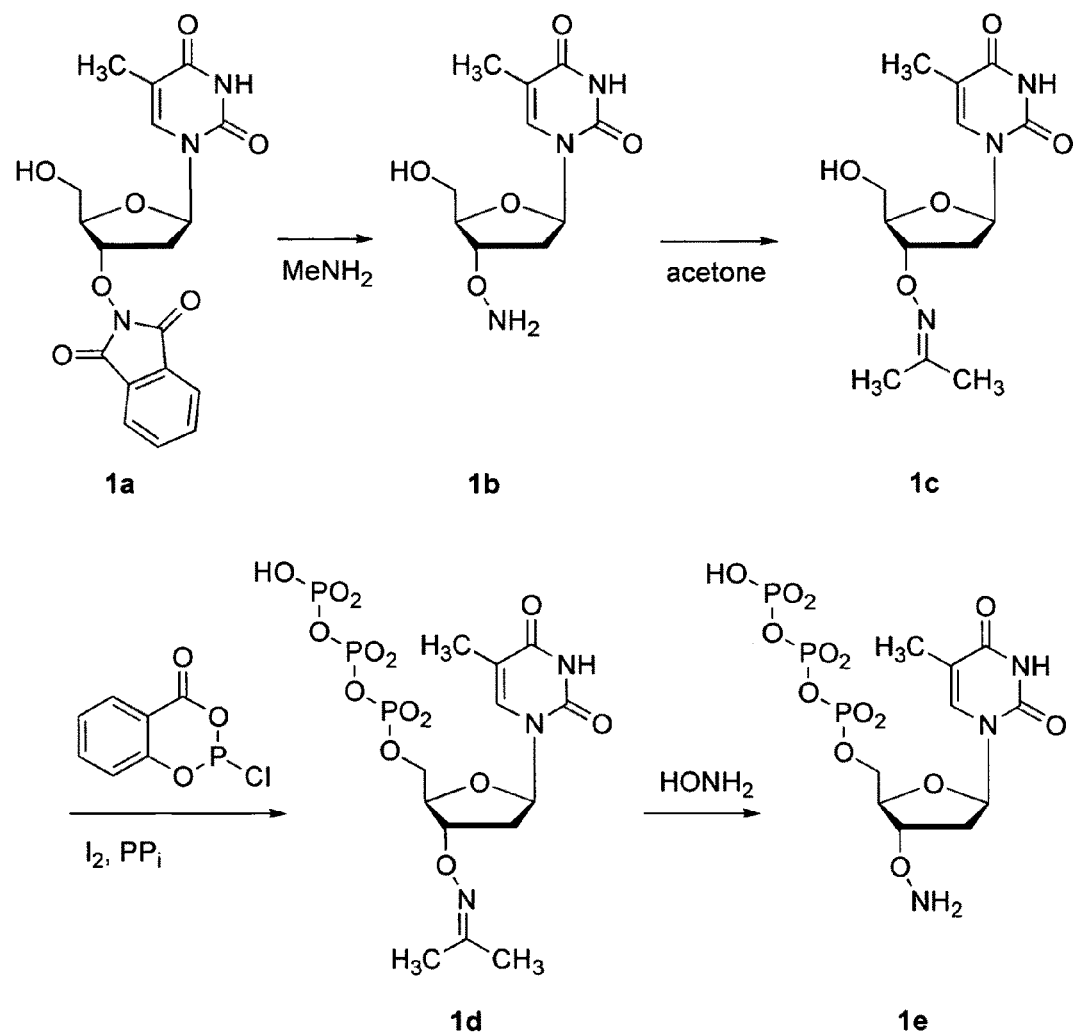
FIG. 2. Example 1. Synthesis of TTP-ONH$_2$.

Synthesis of TTP-ONH$_2$ (FIG. 2)

3'-O—(N-Acetone-oxime)-thymidine (1c)

3'-O-Phthalimido-thymidine (1a), prepared following procedures described in literature [De Clercq, E., Inoue, I., Kondo, K. (1990) Preparation of 3-O-amino-2'-deoxyribonucleoside derivatives as antiviral agents for human retrovirus, particularly human immunodeficiency virus. *Eur. Pat. Appl.* 14 pp] [Kondo, K., Ogiku, T., Inoue, I. (1985) Synthesis of 5'(3')-O-amino nucleosides. *Symp. Nucleic Acids Chem.* 16, 93-96] [Burgess, K., Gibbs, R. A., Metzker, M. L., Raghavachari, R. (1994) Synthesis of an oxyamide linked nucleotide dimer and incorporation into antisense oligonucleotide sequences. *J. Chem. Soc. Chem. Commun.* 8, 915-916] [Cook, P. D., Sanghvi, Y. S. (1994) Preparation of antisense heteroatomic oligonucleotide analogs. *PCT Int. Appl.* 90 pp]. The procedures from these literature citations are specifically incorporated into this specification by citation. This material (1.15 g, 3.0 mmol) was dissolved in aqueous methylamine solution (4%, 22 mL, ca. 24 mmol). After 20 min at room temperature (RT), most of the methylamine was removed in vacuo and the remaining solution was treated with acetone (3 mL). After 3 h at RT, the volatiles were removed in vacuo. The residue was redissolved in a mixture of water (25 mL) and CH$_3$CN (7 mL). Solids were removed from the mixture by filtration (0.2 μm) prior to purification by reverse phase HPLC (Waters Prep Nova-Pak HR C18 column, 60 Å, 19×300 mm, eluent A=25 mM triethylammonium acetate (TEAA) pH 7, eluent B=CH$_3$CN, gradient from 25 to 50% B in A over 7 min, then to 80% B over 8 min, flow rate=5 mL/min, Retention time (Rt)=14 min), which gave 3'-O—(N-acetone-oxime)-thymidine (1c, 640 mg; 72%) as a colorless foam after lyophilization.

$^1$H-NMR (d$_6$-DMSO, 300 MHz): ∂ (ppm)=1.79 (d, J=0.9 Hz, 3H); 1.83 (s, 3H); 1.84 (s, 3H); 2.15-2.35 (m, 2H); 3.55-3.70 (m, 2H); 3.98-4.05 (m, 1H); 4.68-4.72 (m, 1H); 5.15 (br. s, 1H); 6.17 (dd, J=5.7, 8.7 Hz, 1H); 7.76 (d, J=0.9 Hz, 1H); 11.3 (br. s, 1H). $^{13}$C-NMR (d$_6$-DMSO, 75 MHz): ∂ (ppm) =12.3; 15.5; 21.5; 36.4; 61.8; 82.1; 83.9; 84.1; 109.6; 136.0; 150.5; 155.8; 163.7.

3'-O—(N-Acetone-oxime)-thymidine-5'-triphosphate
(1d)

To a solution of 3'-O—(N-acetone-oxime)-thymidine (1c, 300 mg, 1.0 mmol) in pyridine (4 mL) and dioxane (3.4 mL) was added a solution of 2-chloro-4H-1,3,2-benzodioxaphosphorin-4-one (260 mg, 1.4 mmol) in dioxane (2.6 mL) at room temperature. After 10 min, a mixture of tributylammonium pyrophosphate in DMF (0.2 M, 10 mL, 2 mmol) and tributylamine (1.2 mL, 4.8 mmol) were added. After 10 min, a solution of iodine (360 mg, 1.4 mmol) and water (0.56 mL) in pyridine (28 mL) was added. After 20 min, the reaction was quenched by the addition of aqueous Na$_2$SO$_3$ (5%, 0.5 mL) and acetone (0.5 mL). The solvents were removed in vacuo. Water (50 mL) was added and the mixture was filtered (0.2 μm). Purification by ion-exchange HPLC (Dionex BioLC DNAPac PA-100, 22×250 mm, eluent A=water, eluent B=1 M aq. NH$_4$HCO$_3$, gradient from 0 to 25% B in 16 min, flow rate=10 mL/min, Rt=13 min), followed by reverse phase HPLC (Waters Prep Nova-Pak HR C18 column, 60 Å, 9×300 mm, eluent A=25 mM TEAA pH 7, eluent B=50% CH$_3$CN in A, gradient from 0 to 70% B in 20 min, flow rate=5 mL/min, Rt=19 min) gave 3'-O—(N-acetone-oxime)-thymidine-5'-triphosphate as a colorless foam after lyophilization. The yield was determined by UV (260 nm, ext. coeff.=8800 Lmol$^{-1}$ cm$^{-1}$) to be 450 μmmol (45%).

$^1$H-NMR (D$_2$O, 300 MHz): ∂ (ppm, rel to HDO=4.65) =1.75-1.79 (m, 9H); 2.18-2.40 (m, 2H); 4.00-4.15 (m, 2H); 4.22-4.27 (m, 1H); 4.46 (s, 2H); 4.78-4.85 (m, 1H); 6.21 (dd, J=5.7, 9.1 Hz, 1H); 7.67 (s, 1H). $^{31}$P-NMR (D$_2$O, 120 MHz):

∂ (ppm, rel to external $H_3PO_4$=0)=−10.5 (d, J=20.0 Hz, 1P); −11.7 (d, J=20.0 Hz, 1P); −23.3 (t, J=20.0 Hz, 1P).

3'-O-Amino-thymidine-5'-triphosphate (1e)

To a solution of 3'-O—(N-acetone-oxime)-thymidine-5'-triphosphate (1d, 100 μmol) in water (10 mL) was added aqueous sodium acetate buffer (1M, pH 4.0, 2 mL, 2 mmol) and aqueous hydroxylamine solution (50 wt-%, 100 μL, ca. 1.6 mmol). After 2 h at room temperature, the reaction was diluted with water (20 mL) and filtered (0.2 μm). Purification by ion-exchange HPLC (Dionex BioLC DNAPac PA-100, 22×250 mm, eluent A=water, eluent B=1 M aq. $NH_4HCO_3$, gradient from 0 to 30% B in 20 min, flow rate=10 mL/min, Rt=15 min) gave 3'-O-amino-thymidine-5'-triphosphate as a colorless foam after lyophilization. The yield was determined by UV (260 nm, ext. coeff.=8800 $Lmol^{-1} cm^{-1}$) to be 82 μmol (82%).

$^1$H-NMR ($D_2O$, 300 MHz): ∂ (ppm, rel to HDO=4.65) =1.78 (d, J=0.9 Hz, 3H); 2.18-2.29 (m, $^1$H); 2.37-2.46 (m, 1H); 4.01-4.16 (m, 2H); 4.25-4.29 (m, 1H); 4.61-4.63 (m, 1H); 6.17 (dd, J=5.8, 9.0 Hz, 1H); 7.62 (d, J=1.2 Hz, 1H); $^{31}$P-NMR ($D_2O$, 120 MHz): ∂ (ppm, rel to external $H_3PO_4$=0) =−10.8 (d, J=20 Hz, 1P); −11.7 (d, J=20 Hz, 1P); −23.1 (t, J=20 Hz, 1P).

Example 2

Figure 3:
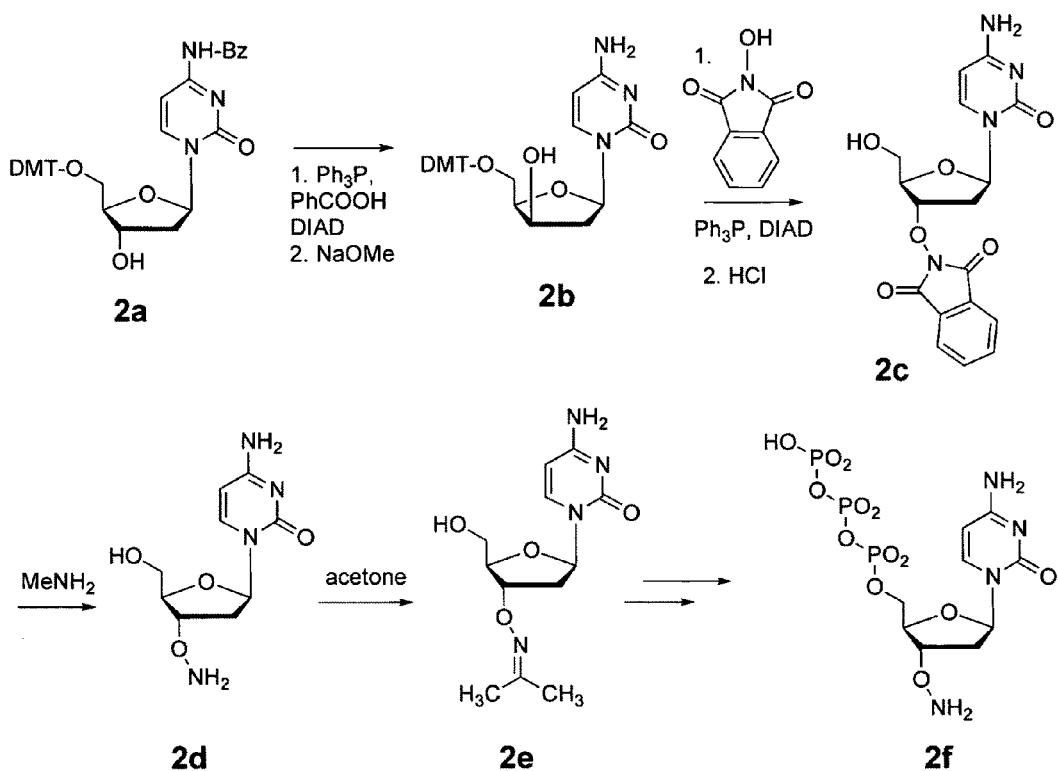
FIG. 3. Example 2. Synthesis of dCTP-ONH$_2$.

Synthesis of dCTP-$ONH_2$ (FIG. 3)

5'-O-Dimethoxytrityl-xylo-2'-deoxycytidine (2b)

To a solution of $N^4$-benzoyl-5'-O-dimethoxytrityl-2'-deoxycytidine (2a, 8.9 g, 14 mmol), benzoic acid (2.5 g, 20 mmol) and triphenylphosphine (5.2 g, 20 mmol) in THF (150 mL) was added DIAD (3.7 mL, 20 mmol) at 0° C. The reaction was allowed to warm to RT overnight and then was quenched by the addition of water (0.5 mL). The solvents were removed in vacuo. Purification by FLC (silica, gradient 50 to 100% EtOAc in hexanes) gave $N^4$-benzoyl-3'-O-benzoyl-5'-O-dimethoxytrityl-xylo-2'-deoxycytidine (13.7 g) as a colorless foam which, according to NMR, contained significant amounts of triphenylphosphine oxide, as well as some elimination product (2',3'-olefin). This intermediate was re-dissolved in MeOH (450 mL) and treated with a solution of sodium methoxide in MeOH (5.3 M, 4 mL, 21 mmol). After 2 h at RT, the reaction was quenched by the addition of AcOH (glacial, 1.25 mL). The solvents were removed in vacuo and the residue was partitioned between $CH_2Cl_2$ (300 mL) and aqueous NaCl (50% sat., 150 mL). The organic phase was separated and the solvent removed in vacuo. Purification by FLC (silica, gradient 5 to 10% MeOH in $CH_2Cl_2$) gave 5'-O-dimethoxytrityl-xylo-2'-deoxycytidine (4.6 g; 62% overall) as a colorless foam.

$^1$H-NMR ($d_6$-DMSO, 300 MHz): ∂ (ppm)=1.78-1.87 (m, 1H); 2.46-2.55 (m, 1H); 3.19-3.24 (m, 1H); 3.37-3.43 (m, 1H); 3.76 (s, 6H); 4.07-4.12 (m, 1H); 4.16-4.19 (m, 1H); 5.10-5.20 (m, 1H); 5.66 (d, J=7.4 Hz, 1H); 6.07 (dd, J=1.7, 7.9 Hz, 1H); 6.86-6.92 (m, 4H); 7.16 (br s, 2H); 7.18-7.48 (m, 9H); 7.68 (d, J=7.4 Hz, 1H). $^{13}$C-NMR ($d_6$-DMSO, 75 MHz): ∂ (ppm)=41.4; 55.0; 62.8; 69.2; 83.4; 85.4; 85.5; 93.0; 113.1; 126.6; 127.8; 129.8; 135.6; 135.7; 141.6; 145.0; 155.2; 158.0; 165.6.

3'-O-Phthalimido-T-deoxycytidine (2c)

To a solution of 5'-O-dimethoxytrityl-xylo-2'-deoxycytidine (2b, 3.4 g, 6.4 mmol), N-hydroxyphthalimide (1.6 g, 10 mmol) and triphenylphosphine (2.6 g, 10 mmol) in THF (180 mL) was added DIAD (1.9 mL, 10 mmol) at 0° C. The reaction was let to warm to RT overnight and then was quenched by the addition of water (0.5 mL). The solvents were removed in vacuo. Purification by FLC (silica, gradient 3 to 10% MeOH in $CH_2Cl_2$) gave 5'-O-dimethoxytrityl-3'-O-phthalimido-2'-deoxycytidine (3.7 g) as a colorless foam which, according to NMR, contained significant amounts of triphenylphosphine oxide and some elimination product (2', 3'-olefin). This intermediate was redissolved in MeOH (150 mL) and treated with aqueous HCl (conc, 7.5 mL) at RT. Within minutes, the product started to precipitate. After 10 minutes, the solids were filtered off and dried at high vacuum to give 3'-O-phthalimido-2'-deoxycytidine (1.5 g, 63% overall) as an off-white powder.

$^1$H-NMR ($d_6$-DMSO, 300 MHz): ∂ (ppm)=2.28-2.38 (m, 1H); 2.65-2.74 (m, 1H); 3.62-3.68 (m, 2H); 4.35-4.40 (m, 1H); 4.95-5.00 (m, 1H); 6.20 (d, J=7.9 Hz, 1H); 6.25 (dd, J=6.9, 7.0 Hz, 1H); 7.89 (s, 4H); 8.22 (d, J=7.9 Hz, 1H); 8.71 (s, 1H); 9.83 (s, 1H). $^{13}$C-NMR ($d_6$-DMSO, 75 MHz): ∂ (ppm)=36.6; 61.0; 84.1; 85.8; 87.7; 94.0; 123.3; 128.6; 134.8; 144.2; 146.9; 159.5; 163.6.

3'-O—(N-Acetone-oxime)-2'-deoxycytidine (2e). 3'-O-Phthalimido-2'-deoxycytidine (2c, 375 mg, 1.0 mmol) was dissolved in aqueous methylamine solution (4%, 11 mL, ca. 12 mmol). After 10 min, most of the methylamine was removed in vacuo, and the remaining solution was treated with acetone (2 mL). After 3 h at RT, the solvent was removed in vacuo. The residue was redissolved in water (30 mL) and the mixture was filtered (0.2 μm). Purification by reverse phase HPLC (Waters Prep Nova-Pak HR C18 column, 60 Å, 19×300 mm, eluent A=25 mM TEAA pH 7, eluent B=$CH_3CN$, gradient from 0 to 50% B in 10 min, then to 85% B in 8 min, flow rate=5 mL/min, Rt=17 min) gave 3'-O—(N-acetone-oxime)-2'-deoxycytidine (2c, 200 mg; 71%) as a colorless foam after lyophilization.

$^1$H-NMR ($d_6$-DMSO, 300 MHz): ∂ (ppm)=1.83 (s, 3H); 1.84 (s, 3H); 1.99-2.09 (m, 1H); 2.30-2.39 (m, 1H); 3.55-3.66 (m, 2H); 4.02-4.06 (m, 1H); 4.65-4.70 (m, 1H); 5.30 (br. s, 1H); 5.77 (d, J=7.4 Hz, 1H); 6.17 (dd, J=5.6, 8.7 Hz, 1H); 7.23 (br. s, 2H); 7.84 (d, J=7.4 Hz, 1H). $^{13}$C-NMR ($d_6$-DMSO, 75 MHz): ∂ (ppm)=15.5; 21.5; 37:3; 61.9; 82.4; 84.2; 85.2; 94.3; 141.0; 155.1; 155.7; 165.6.

3'-O—(N-Acetone-oxime)-2'-deoxycytidine-5'-triphosphate

To a solution of 3'-O—(N-acetone-oxime)-2'-deoxycytidine (2e, 170 mg, 0.6 mmol) in pyridine (2 mL) and dioxane (1.5 mL) was added a solution of 2-chloro-4H-1,3,2-benzodioxaphosphorin-4-one (150 mg, 0.8 mmol) in dioxane (1.5 mL) at RT. After 15 min a mixture of tributylammonium pyrophosphate in DMF (0.2 M, 6 mL, 1.2 mmol) and tributylamine (0.7 mL, 2.8 mmol) was added. After 20 min a solution of iodine (210 mg, 0.8 mmol) and water (0.32 mL) in pyridine (16 mL) was added. After 20 min the reaction was quenched by the addition of aqueous $Na_2SO_3$ (5%, 0.5 mL) and acetone (0.5 mL). The solvents were removed in vacuo. Water (30 mL) was added, and the mixture was filtered (0.2 μm). Purification by ion-exchange HPLC (Dionex BioLC DNAPac PA-100, 22×250 mm, eluent A=water, eluent B=1 M aq. $NH_4HCO_3$, gradient from 0 to 25% B in 16 min, flow rate=10 mL/min, Rt=14 min), followed by reverse phase HPLC (Waters Prep Nova-Pak HR C18 column, 60 Å, 19×300 mm, eluent A=25 mM TEAA pH 7, eluent B=50% $CH_3CN$ in A, gradient from 0 to 70% B in 20 min, flow rate=5 mL/min, Rt=18 min) gave 3'-O—(N-acetone-oxime)-2'-deoxycytidine-5'-triphosphate (not shown in the Figure) as a colorless foam after lyophilization. The yield was determined by UV (260 nm, ext. coeff.=7300 Lmol$^{-1}$ cm$^{-1}$) to be 225 μmol (38%).

$^1$H-NMR (D$_2$O, 300 MHz): ∂ (ppm, rel to HDO=4.65) =1.77 (s, 3H); 1.79 (s, 3H); 2.12-2.22 (m, 1H); 2.40-2.50 (m, 1H); 4.00-4.16 (m, 2H); 4.28-4.33 (m, 1H); 4.76-4.80 (m, 1H); 6.09 (d, J=7.7 Hz, 1H); 6.18 (dd, J=5.7, 8.4 Hz, 1H); 7.23 (br. s, 2H); 7.96 (d, J=7.7 Hz, 1H). $^{31}$P-NMR (D$_2$O, 120 MHz): ∂ (ppm, rel to external H3PO4=0)=−10.9 (d, J=19.5 Hz, 1P); −11.4 (d, J=19.5 Hz, 1P); −23.3 (t, J=19.5 Hz, 1P).

3'-O-Amino-2'-deoxycytidine-5'-triphosphate (2f)

To a solution of 3'-O—(N-acetone-oxime)-2'-deoxycytidine-5'-triphosphate (2e, 100 μmol) in water (10 mL) was added aqueous sodium acetate buffer (1 M, pH 4.0, 2 mL, 2 mmol) and aqueous hydroxylamine solution (50 wt-%, 100 μL, ca. 1.6 mmol). After 2 h at RT, the reaction was diluted with water (20 mL) and filtered (0.2 μm). Purification by ion-exchange HPLC (Dionex BioLC DNAPac PA-100, 22×250 mm, eluent A=water, eluent B=1 M aq. NH$_4$HCO$_3$, gradient from 0 to 30% B in 20 min, flow rate=10 mL/min, Rt=16 min) gave 2f as a colorless foam after lyophilization (74%, by UV, (260 nm, ext. coeff.=7300 Lmol$^{-1}$ cm$^{-1}$). $^1$H-NMR (D$_2$O, 300 MHz): ∂ (ppm, rel to HDO=4.65)=2.09-2.16 (m, 1H); 2.40-2.50 (m, 1H); 4.00-4.10 (m, 2H); 4.25-4.30 (m, 1H); 4.40-4.45 (m, 1H); 6.02 (d, J=6.5 Hz, 1H); 6.14 (dd, J=6.0, 7.9 Hz, 1H); 7.85 (d, J=6.5 Hz, 1H). $^{31}$P-NMR (D$_2$O, 120 MHz): ∂ (ppm, rel to external H$_3$PO$_4$=0)=−10.2 (br, 1P); −11.3 (br, 1P); −22.9 (br, 1P).

Example 3

Figure 4:
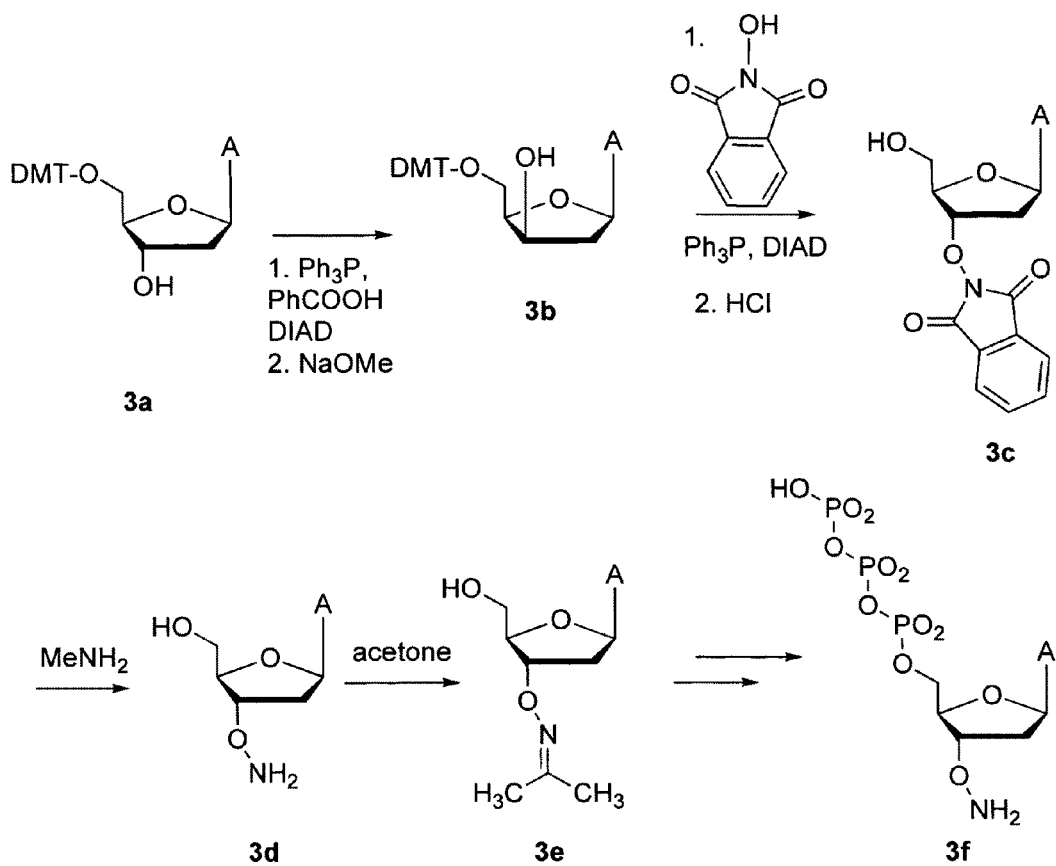
FIG. 4. Example 3. Synthesis of dATP-ONH$_2$.

Synthesis of dATP-ONH$_2$ (FIG. 4)

5'-O-Dimethoxytrityl-xylo-2'-deoxyadenosine (3b)

To a solution of 5'-O-dimethoxytrityl-2'-deoxyadenosine (3a, 8.3 g, 15 mmol), benzoic acid (3.0 g, 24 mmol) and triphenylphosphine (6.5 g, 24 mmol) in THF (250 mL) was added DIAD (4.5 mL, 24 mmol) at RT. After 1 h the reaction was quenched by the addition of MeOH (5 mL). The solvents were removed in vacuo. Purification by FLC (silica, gradient 3 to 5% MeOH in CH$_2$Cl$_2$) gave 3'-O-benzoyl-5'-O-dimethoxytrityl-xylo-2'-deoxyadenosine (12 g) as a colorless foam which, according to NMR, contained some triphenylphosphine oxide as well as some elimination product (2',3'-olefin). This intermediate was redissolved in MeOH (300 mL) and treated with a solution of sodium methoxide in MeOH (5.3 M, 4 mL, 21 mmol). After 16 h at RT, the reaction was quenched by the addition of AcOH (glacial, 1.5 mL). The solvents were removed in vacuo. Purification by FLC (silica, gradient 3 to 10% MeOH in CH$_2$Cl$_2$) gave 5'-O-dimethoxytrityl-xylo-2'-deoxyadenosine (3.7 g; 45% overall) as a colorless foam.

$^1$H-NMR (d$_6$-DMSO, 300 MHz): ∂ (ppm)=2.26-2.34 (m, 1H); 2.74-2.84 (m, 1H); 3.18-3.25 (m, 1H); 3.34-3.42 (m, 1H); 3.70-3.74 (2s, 6H); 4.17-4.22 (m, 1H); 4.31-4.36 (m, 1H); 5.95 (d, J=5.7 Hz, 1H); 6.35 (dd, J=1.0, 7.8 Hz, 1H); 6.77-6.86 (m, 4H); 7.16-7.44 (m, 11H); 8.16 (s, 1H); 8.27 (s, 1H). $^{13}$C-NMR (d$_6$-DMSO, 75 MHz): ∂ (ppm)=40.6; 55.0; 55.0; 63.1; 69.6; 82.9; 83.6; 85.5; 113.1; 119.0; 126.6; 127.7; 127.7; 129.7; 135.6; 135.8; 139.8; 145.0; 148.6; 152.3; 156.1; 158.0; 158.0.

3'-O-Phthalimido-2'-deoxyadenosine (3c)

To a solution of 5'-O-dimethoxytrityl-xylo-2'-deoxyadenosine (3b, 3.4 g, 6 mmol), N-hydroxy-phthalimide (1.6 g, 10 mmol) and triphenylphosphine (2.6 g, 10 mmol) in THF (120 mL) was added DIAD (1.9 mL, 10 mmol) at RT. After 1 h the reaction was quenched by the addition of MeOH (3 mL). The solvents were removed in vacuo. Purification by FLC (silica, gradient 3 to 5% MeOH in CH$_2$Cl$_2$) gave 5'-O-dimethoxytrityl-3'-O-phthalimido-2'-deoxyadenosine (6.2 g) as a colorless foam which, according to NMR, contained significant amounts of triphenylphosphine oxide and some elimination product (2',3'-olefin). This intermediate was redissolved in MeOH (30 mL) and treated with methanolic HCl (1.25 M, 55 mL, ca. 70 mmol) at RT. Within minutes, product started to precipitate. After 10 minutes, solids were removed by filtration and dried at high vacuum to give 3c (1.5 g, 63% overall) as an off-white powder.

$^1$H-1-NMR (d$_6$-DMSO, 300 MHz): ∂ (ppm)=2.62-3.02 (m, 2H); 3.60-3.66 (m, 2H); 4.37-4.41 (m, 1H); 5.13-5.18 (m, 1H); 6.59 (dd, J=6.2, 7.2 Hz, 1H); 7.91 (s, 4H); 8.58 (s, 1H); 8.78 (s, 1H); 8.97 (br s, 1H); 9.60 (br s, 1H). $^{13}$C-NMR (d$_6$-DMSO, 75 MHz): ∂ (ppm)=36.1; 61.2; 83.8; 84.1; 88.0; 118.5; 123.4; 128.7; 134.9; 142.0; 145.2; 148.1; 150.4; 163.8.

3'-O—(N-Acetone-oxime)-2'-deoxyadenosine (3e)

3'-O-Phthalimido-2'-deoxyadenosine (3c, 790 mg, 2.0 mmol) was dissolved in aqueous methylamine solution (4%, 22 mL, ca. 24 mmol). After 20 min, most of the methylamine was removed in vacuo, and the remaining solution was treated with acetone (3 mL). After 3 h at RT, the solvent was removed in vacuo. The residue was redissolved in water (35 mL) and CH$_3$CN (15 mL), and the mixture was filtered (0.2 μm). Purification by reverse phase HPLC (Waters Prep Nova-Pak HR C18 column, 60 Å, 19×300 mm, eluent A=25 mM TEAA pH 7, eluent B=CH$_3$CN, gradient from 25 to 50% B in 7 min, then to 80% B in 8 min, flow rate=5 mL/min, Rt=14 min) gave 3'-O—(N-acetone-oxime)-2'-deoxyadenosine (465 mg; 76%) as a colorless foam after lyophilization.

$^1$H-1-NMR (d$_6$-DMSO, 300 MHz): ∂ (ppm)=1.86 (s, 3H); 1.87 (s, 3H); 2.47-2.55 (m, 1H); 2.82-2.93 (m, 1H); 3.54-3.72 (m, 2H); 4.11-4.16 (m, 1H); 4.81-4.85 (m, 1H); 5.43 (dd, J=4.7, 7.0 Hz, 1H); 6.33 (dd, J=5.9, 8.9 Hz, 1H); 7.34 (br. s, 2H); 8.13 (s, 1H); 8.35 (s, 1H). $^{13}$C-NMR (d$_6$-DMSO, 75 MHz): ∂ (ppm)=15.5; 21.5; 36.4; 62.2; 82.5; 84.4; 84.9; 119.3; 139.6; 148.8; 152.3; 155.9; 156.2.

3'-O—(N-Acetone-oxime)-2'-deoxyadenosine-5'-triphosphate

To a suspension of 3'-O—(N-acetone-oxime)-2'-deoxyadenosine (3e, 180 mg, 0.6 mmol) in pyridine (2 mL), dioxane (1.5 mL) and DMF (1 mL) was added a solution of 2-chloro-4H-1,3,2-benzodioxaphosphorin-4-one (150 mg, 0.8 mmol) in dioxane (1.5 mL) at RT, leading to a clear solution. After 15 mM a mixture of tributylammonium pyrophosphate in DMF (0.2 M, 6 mL, 1.2 mmol) and tributylamine (0.7 mL, 2.8 mmol) was added. After 20 mM a solution of iodine (210 mg, 0.8 mmol) and water (0.32 mL) in pyridine (16 mL) was added. After 20 mM, the reaction was quenched by the addition of aqueous Na$_2$SO$_3$ (5%, 0.5 mL) and acetone (0.5 mL). The solvents were removed in vacuo. Water (40 mL) was added, and the mixture was filtered (0.2 μm). Purification by ion-exchange HPLC (Dionex BioLC DNAPac PA-100, 22×250 mm, eluent A=water, eluent B=1 M aq. NH$_4$HCO$_3$, gradient from 0 to 25% B in 16 mM, flow rate=10 mL/min, Rt=13 mM), followed by reverse phase HPLC (Waters Prep Nova-Pak HR C18 column, 60 Å, 19×300 mm, eluent A=25 mM TEAA pH 7, eluent B=50% CH$_3$CN in A, gradient from 0 to 100% B in 20 mM, flow rate=5 mL/min, Rt=18 min) gave 3'-O—(N-acetone-oxime)-2'-deoxyadenosine-5'-triphosphate as a colorless foam after lyophilization. The yield was determined by UV (260 nm, ext. coeff.=15400 Lmol$^{-1}$ cm$^{-1}$) to be 240 μmol (40%).

$^1$H-NMR (D$_2$O, 300 MHz): ∂ (ppm, rel to HDO=4.65) =1.78 (s, 3H); 1.83 (s, 3H); 2.55-2.78 (m, 2H); 3.97-4.13 (m, 2H); 4.32-4.37 (m, 1H); 4.90-4.95 (m, 1H); 6.33 (dd, J=5.8, 9.0 Hz, 1H); 8.03 (s, 1H); 8.37 (s, 1H). $^{31}$P-NMR (D$_2$O, 120 MHz): ∂ (ppm, rel to external H$_3$PO$_4$=0)=−10.4 (d, J=19.5Hz, 1P); −11.4 (d, J=19.5 Hz, 1P); −23.2 (t, J=19.5Hz, 1P). 3'-O-Amino-2'-deoxyadenosine-5'-triphosphate (3f).

To a solution of 3'-O—(N-acetone-oxime)-2'-deoxyadenosine-5'-triphosphate (100 μmol) in water (10 mL) was added aqueous sodium acetate buffer (1M, pH 4.0, 2 mL, 2 mmol) and aqueous hydroxylamine solution (50 wt-%, 100 μL, ca. 1.6 mmol). After 2 h at RT, the reaction was diluted with water (20 mL) and filtered (0.2 μm). Purification by ion-exchange HPLC (Dionex BioLC DNAPac PA-100, 22×250 mm, eluent A=water, eluent B=1 M aq. NH$_4$HCO$_3$, gradient from 0 to 30% B in 20 min, flow rate=10 mL/min, Rt=15 min) gave 3f as a colorless foam after lyophilization. The yield was determined by UV (260 nm, ext. coeff.=15400 Lmol$^{-1}$ cm$^{-1}$) to be 65 μmol (65%).

$^1$H-NMR (D$_2$O, 300 MHz): ∂ (ppm, rel to HDO=4.65) =2.36-2.43 (m, 1H); 2.57-2.63 (m, 1H); 3.93-4.10 (m, 2H); 4.29-4.34 (m, 1H); 4.50-4.54 (m, 1H); 6.28 (dd, J=7.0, 8.0 Hz, 1H); 8.04 (s, 1H); 8.33 (s, 1H). $^{31}$P-NMR (D$_2$O, 120 MHz): ∂ (ppm, rel to external H$_3$PO$_4$=0)=−8.8 (d, J=19.5 Hz, 1P); −11.2 (d, J=19.5 Hz, 1P); −22.6 (t, J=19.5 Hz, 1P).

Example 4

Figure 5:
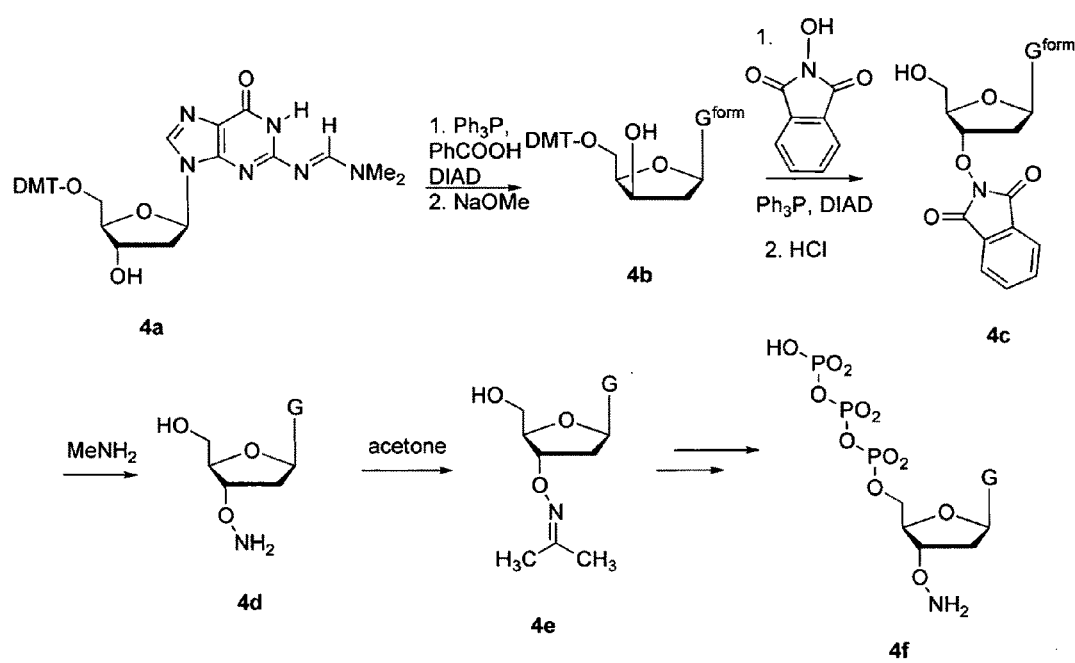
FIG. 5. Example 4. Synthesis of dGTP-ONH$_2$.

Synthesis of dGTP-ONH$_2$ (FIG. 5)

5'-O-Dimethoxytrityl-N2-dimethylaminomethylidene-xylo-2'-deoxyguanosine (4b)

To a solution of 5'-O-dimethoxytrityl-N2-dimethylaminomethylidene-2'-deoxyguanosine (4a, 9.4 g, 15 mmol), benzoic acid (3.0 g, 24 mmol) and triphenylphosphine (6.5 g, 24 mmol) in THF (250 mL) was added DIAD (4.5 mL, 24 mmol) at RT. After 30 min the reaction was quenched by the addition of MeOH (2 mL). The solvents were removed in vacuo. This intermediate was redissolved in MeOH (600 mL) and treated with a solution of sodium methoxide in MeOH (5.3 M, 7.6 mL, 40 mmol). After 16 h at RT, the reaction was quenched by the addition of AcOH (glacial, 2.3 mL, 40 mmol). The solvents were removed in vacuo. Purification by FLC (silica, gradient 0 to 10% MeOH in CH$_2$Cl$_2$) gave 5'-O-dimethoxytrityl-N2-dimethylaminomethylidene-xylo-2'-deoxyguanosine (5.6 g; 50% overall) as a colorless foam.

$^1$H-NMR (d$_6$-DMSO, 300 MHz): ∂ (ppm)=2.18-2.26 (m, 1H); 2.69-2.80 (m, 1H); 3.03 (s, 3H); 3.11 (s, 3H); 3.19-3.25 (m, 1H); 3.34-3.40 (m, 1H); 3.70-3.74 (2s, 6H); 4.16-4.20 (m, 1H); 4.32-4.37 (m, 1H); 5.57-5.61 (m, 1H); 6.29 (dd, J=1.5, 8.4 Hz, 1H); 6.80-6.86 (m, 4H); 7.16-7.44 (m, 9H); 8.00 (s, 1H); 8.54 (s, 1H); 11.38 (s, 1H). $^{13}$C-NMR (d$_6$-DMSO, 75 MHz): ∂ (ppm)=34.6; 40.6; 40.9; 55.0; 55.0; 63.2; 69.4; 82.0; 83.5; 85.5; 113.1; 119.4; 126.6; 127.7; 129.7; 129.8; 135.6; 135.7; 137.3; 145.0; 149.4; 157.3; 157.7; 157.9; 158.0; 158.0.

5'-O-Dimethoxytrityl-N2-dimethylaminomethylidene-3'-O-phthalimido-2'-deoxyguanosine (4c)

To a solution of 5'-O-dimethoxytrityl-N2-dimethylaminomethylidene-xylo-2'-deoxyguanosine (4.7 g, 7.5 mmol), N-hydroxy-phthalimide (2.1 g, 13 mmol) and triphenylphosphine (3.4 g, 13 mmol) in THF (150 mL) was added DIAD (2.5 mL, 13 mmol) at RT. After 1 h the reaction was quenched by the addition of MeOH (2 mL). The solvents were removed in vacuo. Purification by FLC (silica, gradient 3 to 10% MeOH in CH$_2$Cl$_2$) gave 5'-O-dimethoxytrityl-N2-dimethylaminomethylidene-3'-O-phthalimido-2'-deoxyguanosine (5.3 g) as a colorless foam which, according to NMR, contained ca 0.25 equivalents of elimination product (2',3'-olefin). An analytical sample was repurified by reverse phase HPLC (Waters Prep Nova-Pak HR C18 column, 60 Å, 19×300 mm, eluent A=25 mM TEAA pH 7, eluent B=CH$_3$CN, gradient from 50% to 90% B in 18 min, then constant 90% B for 6 min, flow rate=5 mL/min, Rt=22 min) to give a colorless foam after lyophilization.

$^1$H-1-NMR (CDCl$_3$, 300 MHz): ∂ (ppm)=2.64-2.74 (m, 1H); 2.84-2.94 (m, 1H); 3.09 (s, 3H); 3.16 (s, 3H); 3.31-3.45 (m, 2H); 3.75 (s, 6H); 4.56-4.61 (m, 1H); 5.12-5.16 (m, 1H); 6.53 (dd, J=5.5, 8.6 Hz, 1H); 6.72-6.78 (m, 4H); 7.12-7.36 (m, 10H); 7.72-7.85 (m, 5H); 8.67 (s, 1H); 10.11 (s, 1H). $^{13}$C-NMR (CDCl$_3$, 75 MHz): ∂ (ppm)=35.3; 41.5; 55.3; 63.6; 82.6; 83.6; 86.7; 88.7; 113.3; 120.4; 123.9; 127.0; 128.0; 128.1; 128.7; 130.0; 130.1; 135.0; 135.5; 135.9; 144.4; 150.4; 157.1; 158.5; 158.6; 158.6; 164.0.

3'-O—(N-acetone-oxime)-2'-deoxyguanosine (4e). To a solution of 5'-O-dimethoxytrityl-N-2-dimethylaminomethylidene-3'-O-phthalimido-2'-deoxyguanosine (4c, 900 mg, ca. 1 mmol phthalimido-compound, contains ca. 0.25 eq. 2',3'-olefin) in MeOH (7 mL) was added aqueous HCl (conc, 0.4 mL, ca 5 mmol) and TFA (0.1 mL, ca 1.5 mmol). The mixture was shaken for 5 min at RT, leading to a clear solution. Ammonium hydroxide (30%, 5 mL, ca 80 mmol) was added, and the resulting suspension was stirred for 1 h. Aqueous methylamine solution (10%, 13 mL, ca. 36 mmol) was added. After 20 min, the supernatant was filtered off and most of the methylamine and ammonia was removed in vacuo. The remaining solution was neutralized with dilute aqueous HCl and treated with acetone (3 mL) and CH$_3$CN (5 mL). After 3 h at RT, the mixture was diluted with water (20 mL) and CH$_3$CN (20 mL) and filtered (0.2 μm). Purification by reverse phase HPLC (Waters Prep Nova-Pak HR C18 column, 60 Å, 19×300 mm, eluent A=25 mM TEAA pH 7, eluent B=CH$_3$CN, gradient from 25 to 50% B in 5 min, then to 80% B in 12 min, flow rate=5 mL/min, Rt=13 min) gave 3'-O—(N-acetone-oxime)-2'-deoxyguanosine (120 mg; 37%) as a colorless foam after lyophilization.

$^1$H-NMR (d$_6$-DMSO, 300 MHz): ∂ (ppm)=1.84 (s, 3H); 1.85 (s, 3H); 2.41-2.50 (m, 1H); 2.62-2.72 (m, 1H); 3.52-3.64 (m, 2H); 4.02-4.08 (m, 1H); 4.74-4.78 (m, 1H); 5.05-5.12 (m, 1H); 6.09 (dd, J=5.7, 8.9 Hz, 1H); 6.51 (br. s, 2H); 7.95 (s, 1H); 10.60 (br. s, 1H).

3'-O—(N-acetone-oxime)-2'-deoxyguanosine-5'-triphosphate. To a suspension of 3'-O—(N-acetone-oxime)-2'-deoxyguanosine (100 mg, 0.3 mmol) in pyridine (1 mL), dioxane (0.8 mL) and DMF (1 mL) was added a solution of 2-chloro-4H-1,3,2-benzodioxaphosphorin-4-one (75 mg, 0.4 mmol) in dioxane (0.75 mL) at RT, leading to a clear solution. After 15 min a mixture of tributylammonium pyrophosphate in DMF (0.2 M, 3 mL, 0.6 mmol) and tributylamine (0.35 mL, 1.4 mmol) was added. After 20 min a solution of iodine (100 mg, 0.4 mmol) and water (0.16 mL) in pyridine (8 mL) was added. After 20 min the reaction was quenched by the addition of aqueous Na2SO3 (5%, 0.5 mL) and acetone (0.5 mL). The solvents were removed in vacuo. Water (30 mL) was added, and the mixture was filtered (0.2 gm). Purification by ion-exchange HPLC (Dionex BioLC DNAPac PA-100, 22×250 mm, eluent A=water, eluent B=1 M aq. NH4HCO3, gradient from 0 to 25% B in 16 min, flow rate=10 mL/min, Rt=16 min), followed by reverse phase HPLC (Waters Prep Nova-Pak HR C18 column, 60 Å, 19×300 mm, eluent A=25 mM TEAA pH 7, eluent B=50% CH3CN in A, gradient from 0 to 100% B in 20 min, flow rate=5 mL/min, Rt=18 min) gave 3'-O—(N-acetone-oxime)-2'-deoxyguanosine-5'-triphosphate as a colorless foam after lyophilization. The yield was determined by UV (260 nm, ext. coeff.=11700 Lmol$^{-1}$ cm$^1$) to be 135 µmol (45%).

$^1$H-NMR (D$_2$O, 300 MHz): ∂ (ppm, rel to HDO=4.65) =1.78 (s, 3H); 1.81 (s, 3H); 2.45-2.55 (m, 1H); 2.65-2.80 (m, 1H); 4.00-4.13 (m, 2H); 4.27-4.32 (m, 1H); 4.87-4.92 (m, 1H); 6.14 (dd, J=5.8, 9.0 Hz, 1H); 7.98 (s, 1H). $^{31}$P-NMR (D$_2$O, 120 MHz): ∂ (ppm, rel to external H$_3$PO$_4$=0)=−9.7 (d, J=19.5 Hz, 1P); −11.4 (d, J=19.5 Hz, 1P); −23.1 (t, J=19.5 Hz, 1P).

3'-O-Amino-2'-deoxyguanosine-5'-triphosphate (4f). To a solution of 3'-O—(N-acetone-oxime)-2'-deoxyguanosine-5'-triphosphate (50 µmol) in water (5 mL) was added aqueous sodium acetate buffer (1M, pH 4.0, 1 mL, 1 mmol) and aqueous hydroxylamine solution (50 wt-%, 50 µL, ca. 0.8 mmol). After 2 h at RT, the reaction was diluted with water (10 mL) and filtered (0.2 µm). Purification by ion-exchange HPLC (Dionex BioLC DNAPac PA-100, 22×250 mm, eluent A=water, eluent B=1 M aq. NH$_4$HCO$_3$, gradient from 0 to 30% B in 20 min, flow rate=10 mL/min, Rt=18 min) gave 3'-O-amino-2'-deoxyguanosine-5'-triphosphate as a colorless foam after lyophilization. The yield was determined by UV (260 nm, ext. coeff.=11700 Lmol$^{-1}$ cm$^{-1}$) to be 36 µmol (72%).

$^1$H-1-NMR (D$_2$O, 300 MHz): ∂ (ppm, rel to HDO=4.65) =2.50-2.75 (m, 2H); 3.97-4.13 (m, 2H); 4.29-4.34 (m, 1H); 4.55-4.60 (m, 1H); 6.08-6.16 (m, 1H); 8.00 (s, 1H). $^{31}$P-NMR (D$_2$O, 120 MHz): a (ppm, rel to external H$_3$PO$_4$=0)=−10.6 (br, 1P); −11.2 (br, 1P); −23.0 (br, 1P).

Example 5

Figure 6:
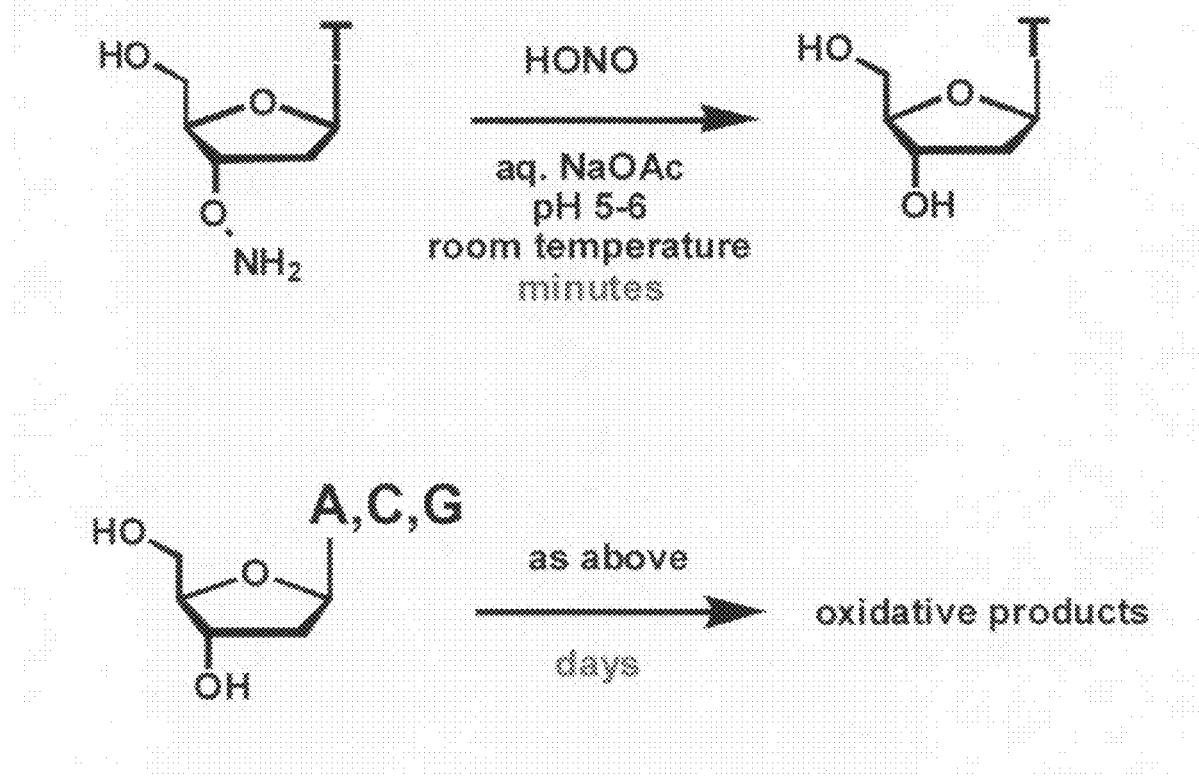
FIG. 6. Example 5. Schematic showing the chemistry behind the process for the rapid and mild removal of the —ONH$_2$ group without damaging the oligonucleotide.
Figure 7:
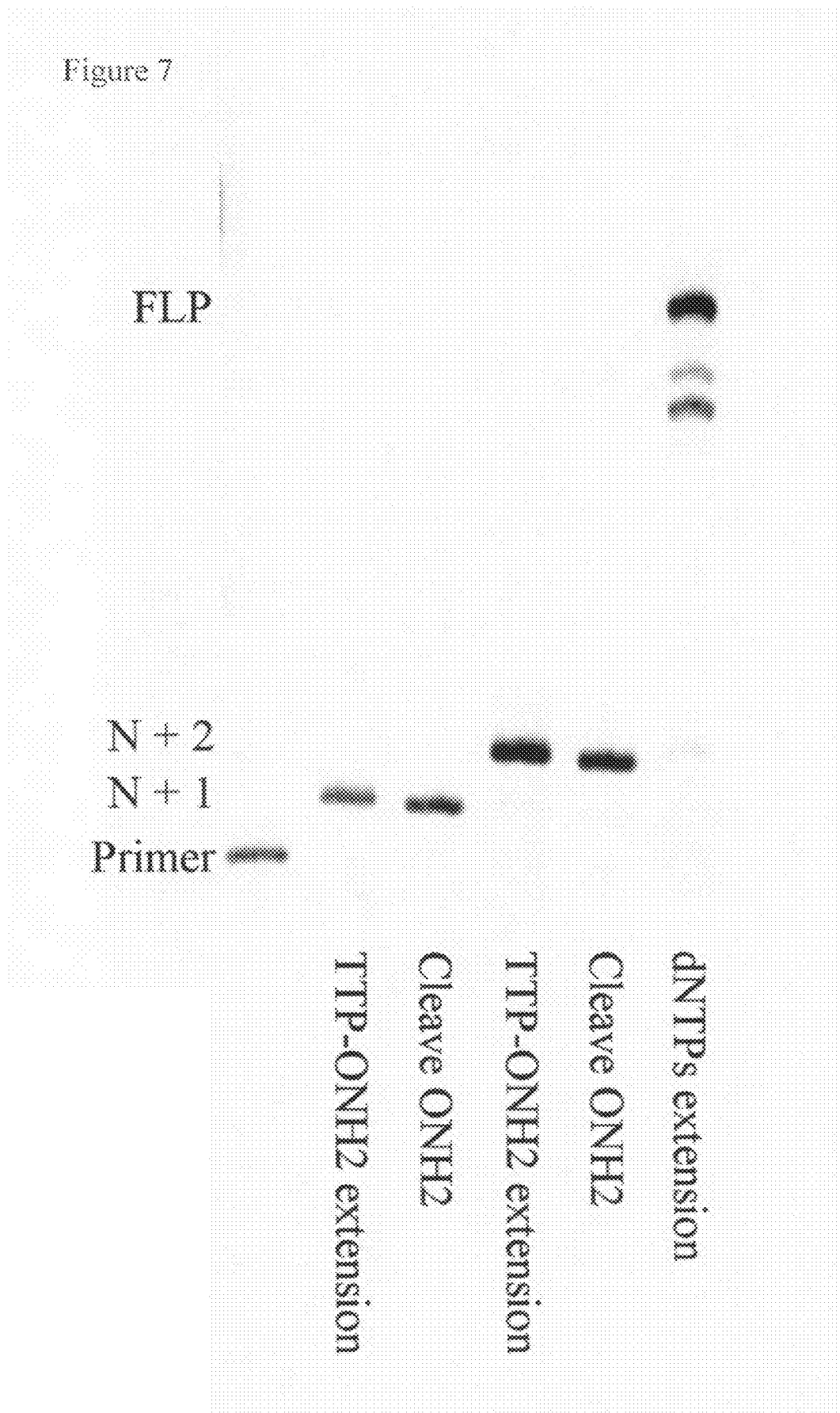
FIG. 7. Example 5. Gel demonstrating the stopping and restarting of primer extension using reversible termination and the rapid and mild removal of an —ONH$_2$ group.

Mild Method for Cleaving a Reversible Terminator and Resuming Primer Extension (FIGS. 6 and 7)

(a) Cleavage of O-(4-nitrobenzyl)hydroxylamine with Aqueous HONO at Varying Dielectric To an aqueous solution of O-(4-nitrobenzyl)hydroxylamine (1 mM, 300 µL) were added "co-solvent" (brine or water or ethanol or isopropanol or acetonitrile or 1,4-dioxane) (500 µL), aqueous sodium acetate buffer (1 M, 100 µL, pH 3.5 to 6.0), and aqueous sodium nitrite solution (100 mM, 100 µL). The resulting pH was measured with a microelectrode (accuracy ca. ±0.02). After 1 h at RT, an aliquot (100 µL) was removed, neutralized by the addition of K-phosphate buffer (170 mM, 600 µL, pH 7), and analyzed by analytical reverse-phase HPLC (Waters NovaPak C-18 4 µm, 3.9×150 mm, with guard column Waters NovaPak C-18 4 µm, 3.9×15 mm, eluent A=3% acetonitrile in 25 mM TEAA pH 7, eluent B=acetonitrile, gradient from 20% B to 50% B in 30 min, flow rate=0.5 mL/min, Rt=product: 8.5 min; starting material: 9.5 mM.).

(b1) Cleavage of 3'-O-aminothymidine 1b with Aqueous HONO and Dioxane as Cosolvent To an aqueous solution of 3'-O-aminothymidine (1b, 20 mM, 50 µL) were added dioxane (300 µL) and aqueous nitrous acid (1 M, 700 µL, pH 5.0 to 6.0, prepared from sodium nitrite and 1 M NaOAc buffer). The resulting pH was measured with a microelectrode (accuracy ca. ±0.02). After 5 min at room temperature, an aliquot (100 µL) was removed, neutralized by the addition of K-phosphate buffer (1 M, 600 µL, pH 7), and analyzed by analytical reverse-phase HPLC (Waters Nova-Pak C-18 4 µm, 3.9×150 mm, with guard column Waters NovaPak C-18 4 µm, 3.9×15 mm, eluent A=25 mM TEAA pH 7, eluent B=acetonitrile, gradient from 3% B to 13% B in 20 min, flow rate=0.5 mL/min, Rt=product: 8 min; starting material: 11 min.). The amount of cleavage was determined by integrating (267 nm) the peaks of the remaining 1b and the product (thymidine). The rates are as follows:

(b) Cleavage of 3'-O-aminothymidine 1b with Aqueous HONO and No Cosolvent

To an aqueous solution of 3'-O-aminothymidine (1b, 20 mM, 2 µL) was added aqueous nitrous acid (350-700 mM NaNO$_2$/1 M NaOAc, 50 µL, pH 5.5-5.75). The resulting pH was measured with a microelectrode (accuracy ca. ±0.02). After 1 or 2 min at room temperature, the reaction was quenched by the addition of K-phosphate buffer (1 M, 200 µL, pH 7), and analyzed by analytical reverse-phase HPLC (Waters NovaPak C-18 4 µm, 3.9×150 mm, with guard column Waters NovaPak C-18 4 µm, 3.9×15 mm, eluent A=25 mM TEAA pH 7, eluent B=acetonitrile, gradient from 3% B to 13% B in 20 min, flow rate=0.5 mL/min, Rt=product: 8 min; starting material: 11 min.). The amount of cleavage was determined by integrating (267 nm) the peaks of the remaining 1b and the product (thymidine). The rates are as follows: As control, the natural nucleosides were treated as follows: An aqueous solution of 2'-deoxyguanosine or 2'-deoxyadenosine or 2'-deoxycytidine (20 mM, 30 µL) was treated with aqueous nitrous acid (700 mM NaNO$_2$, 1 M NaOAc, pH 5.5, 500 µL) at room temperature for 72 h (i.e. 4320 min). An aliquot (50 µL) was removed, neutralized by the addition of K-phosphate buffer (1 M, 200 µL, pH 7), and analyzed by analytical reverse-phase HPLC (Waters NovaPak C-18 4 µm, 3.9×150 mm, with guard column Waters NovaPak C-18 4 µm, 3.9×15 mm. eluent A=25 mM TEAA pH 7, eluent B=acetonitrile, gradient from 0% B to 3% B in 10 min, then to 30% B in 20 min, flow rate=0.5 mL/min, R$_f$=dG: 14 min, dA: 18 min, dC: 8 min). The amount of decomposition was determined by integrating (260 nm) the peaks of the remaining starting material (nucleoside) and the product(s). The results are as follows:

| [HONO] mM | pH | cleavage 1 min | cleavage 2 min |
|---|---|---|---|
| 350 | 5.50 | n/a | 90% |
| 700 | 5.50 | 98% | >99% |
| 700 | 5.65 | n/a | 96% |

| nucleoside 72 h | oxidation 2 min | oxidation (extrapolated) |
|---|---|---|
| dG | 20% | <1/10000 |
| dA | 13% | <1/10000 |
| dC | 15% | <1/10000 |

Addition of the 3'-ONH$_2$ Reversible Terminator Followed by Cleavage and Continued Extension
SEQ ID 1 5'-GCGTAATACGACTCACTATGGACG
SEQ ID 2 3'-CGCATTATGCTGAGTGATACCTGCAAT-GTGCTTCTG-5'

A 5'-biotinylated template SEQ ID 2 (30 pmol) was annealed to the complementary 5'-$^{32}$P-labeled primer SEQ ID 1 (2.5 pmol) and cold primer SEQ ID 1 (22.5 pmol) (both prepared by Integrated DNA Technologies). The duplex was then immobilized onto magnetic beads loaded with streptavidin (Dynabeads M-270 Streptavidin, Dynal Biotech). All subsequent reactions were done on the magnetic beads.

To determine whether HONO could cleave the 3'-terminal ONH$_2$ group from a template-bound oligonucleotide and permit subsequent primer extension in a cycle of the type needed for sequencing using cyclic reversible termination, a 5'-biotinylated template that called for incorporation of two consecutive T's opposite the two consecutive template A's was used. Streptavidin on magnetic beads was used to recover products. In the first cycle, beads were incubated (72° C., 2 min) with PD-58 polymerase in the presence of T-ONH$_2$ triphosphate (100 µM). Then, the products were treated with buffered sodium nitrite/HONO to cleave the —ONH$_2$ group, generating a free 3'-OH group. The cleavage buffer was removed and the beads were washed twice (500 µL of 2% HONH$_2$) FIG. 7 shows the results produced by an extension-cleavage-extension-cleavage cycle. Both primer extension and termination were observed to give clean N+1 products upon incubation in for the first extension step of the cycle. This was indicated by a slower moving band arising from the reversibly terminated N+1 product.

Treatment of that product on magnetic beads with buffered HONO/nitrite (20 min) cleanly removes the 3'-ONH$_2$ group, as indicated by the generation of a product that moves slightly faster than the 3'-ONH$_2$ terminated product. This increased mobility is interpreted as a consequence of either a slightly smaller molecule arising from the replacement of a more bulky —NH$_2$ group by a smaller —H group, or the consequence of a slightly more anion product arising from the replacement of a slightly cationic —ONH$^+_3$ group (pK$_a$~6) by an uncharged —OH group. To demonstrate that the cycle could be repeated, another cycle was run to generate the N+2 product having a 3'-ONH$_2$ blocking group, which again migrates slower than the N+1 product (FIG. 7). Cleavage with buffered HONO/nitrite again generates a product that moves slightly faster. This product is then extended to full length product by adding all dNTPs; pausing bands observed late in the extension were attributed to the presence of a biotin at 5'-end of the template blocked the primer extension to some extent.

Example 6

Screening Polymerases for Incorporation of the Reversibly and Irreversibly Blocked 3'-ONH$_2$ thymidine-5'-triphosphate (FIGS. 8, 9, 10A and 10B)

Figure 8:
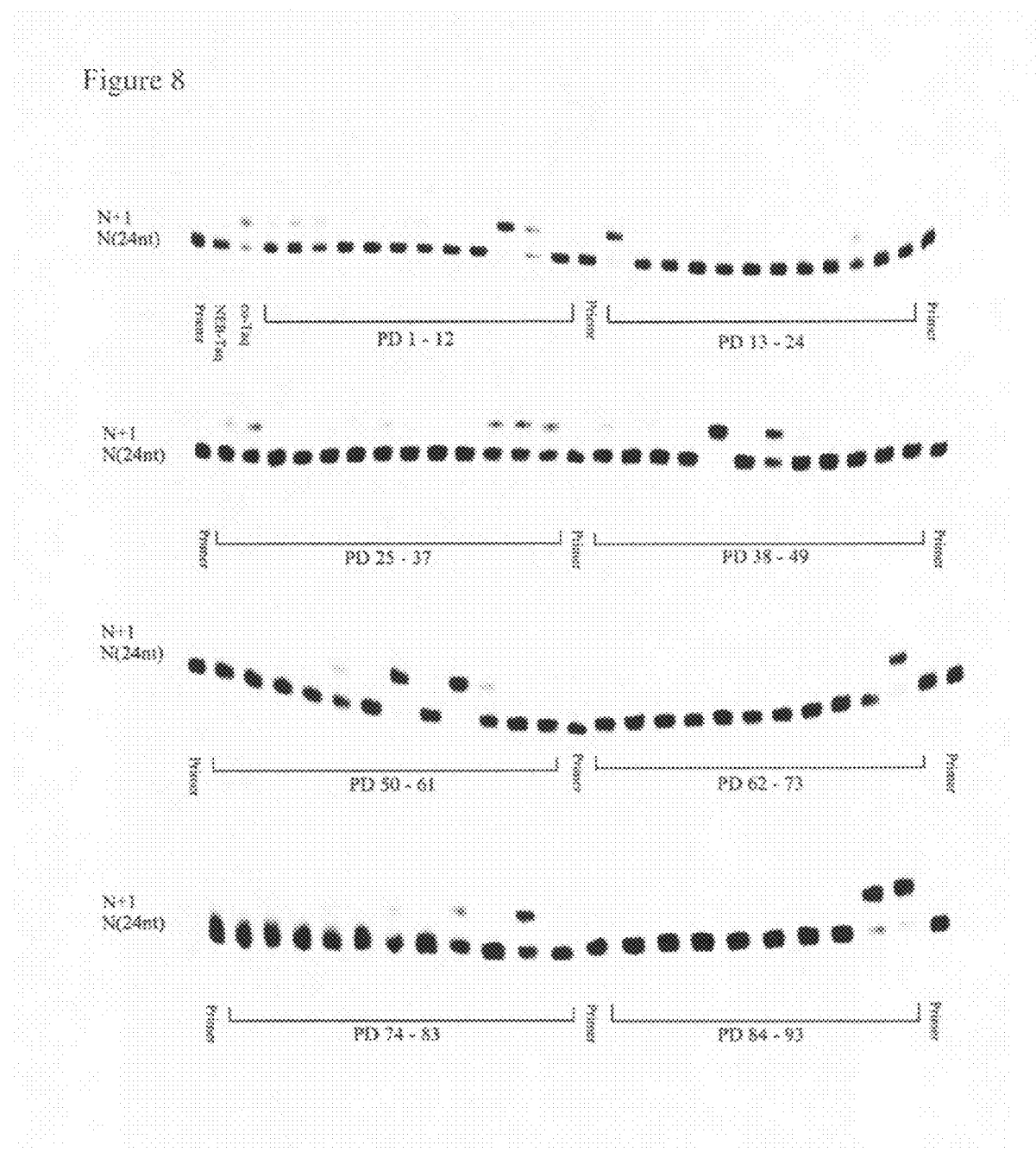
FIG. 8. Example 6. Incorporation of the reversibly blocked 3'-ONH$_2$ thymidine-5'-triphosphate by the Taq variants of a phylogenetically designed (PD) library.

Primer and Template
SEQ ID 1 5'-GCGTAATACGACTCACTATGGACG-3'
SEQ ID 2 3'-CGCATTATGCTGAGTGATACCTGCAAT-GTGCTTCTG-5'
Standing Start Primer-Extension Assays Gamma-$^{32}$P-labeled primer SEQ ID 1 (2.5 pmol), cold primer SEQ ID 1 (22.5 pmol) and template SEQ ID 2 (30 pmol) were annealed by incubation at 95° C. for 5 mM in NEB ThermoPol Reaction Buffer (20 mM Tris-HCl, 10 mM KCl, 10 mM (NH$_4$)$_2$SO$_4$, 2 mM MgSO$_4$, 0.1% TritonX-100) and slowly cooled to room temperature, followed by the addition of Taq cell-free extract (4 µL, the sole source of polymerase). Then, the mixture (final volume 10 µL) was pre-heated to 72° C. (30 sec), and the extension was initiated by adding either reversibly terminated or irreversibly terminated nucleoside triphosphates (final concentration of 100 µM) or both. After 2 mM, the reaction was quenched by 10 mM EDTA in formamide loading buffer (20 µL) and was resolved on a 14% PAGE (FIGS. 8 and 9).

Incorporation of 3'-modified 2'-deoxynucleoside thymidine triphosphates by Taq Polymerase Variants of PD Library 93 Taq polymerase variants from PD library (Table 1) were tested for their ability to incorporate TTP-ONH$_2$. Co-Taq polymerase and the Taq polymerase from New England Biolabs were also tested in parallel as controls. The data in FIG. 8 showed that 30 variant polymerases (32.3% of the PD library mutants) were able to incorporate TTP-ONH$_2$ better than NEB Taq, which generated at most a trace of N+1 product upon incorporation with the triphosphate at 72° C. Of these variants, eight extended the primer by more than 50% to N+1, performing better than Co-Taq. The absence of an obvious N+2 band in FIG. 8 indicated that the 3'-ONH$_2$ group, once appended at the 3'-end of the primer by incorporation of the deoxynucleoside triphosphate carrying it, successfully terminate primer extension. In particular, PD-42 (A597T, L616A, F667Y, E745H) and PD-58 (E520G, K540I, L616A respectively) showed the best incorporation of dTTP-ONH$_2$.

Figure 9:
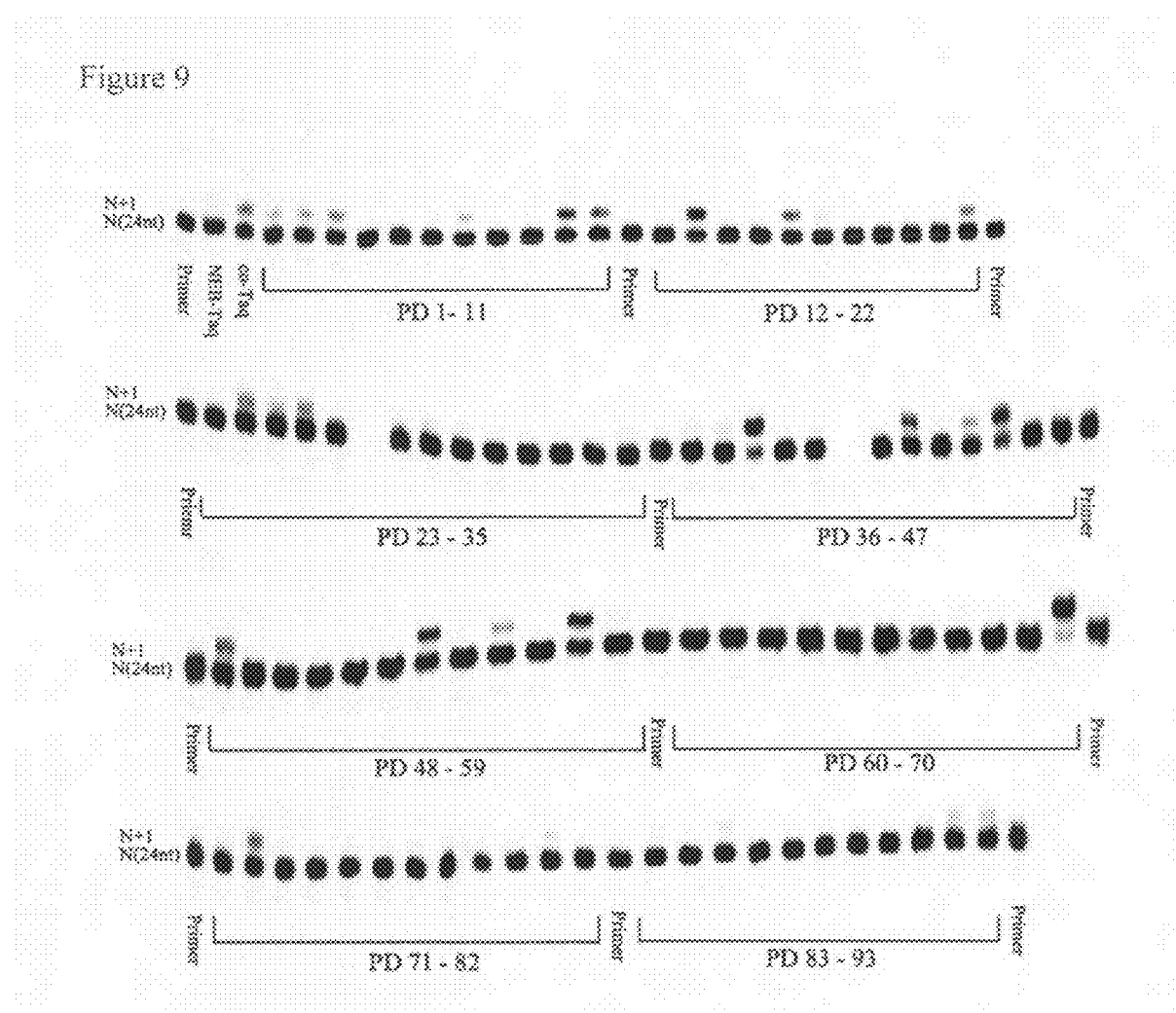
FIG. 9. Example 6. Incorporation of the irreversibly blocked 2',3'-dideoxythymidine-5'-triphosphate by the Taq variants of PD library.

To explore the potential of these variant polymerases to incorporate the corresponding 2'-, 3'-dideoxynucleotide, they were challenged with ddTTP (FIG. 9). A total of 27 variant polymerases were able to incorporate ddTTP to a detectable extent, while three of these variants converted more than 50% of the primer to n+1 product.

Figure 10:
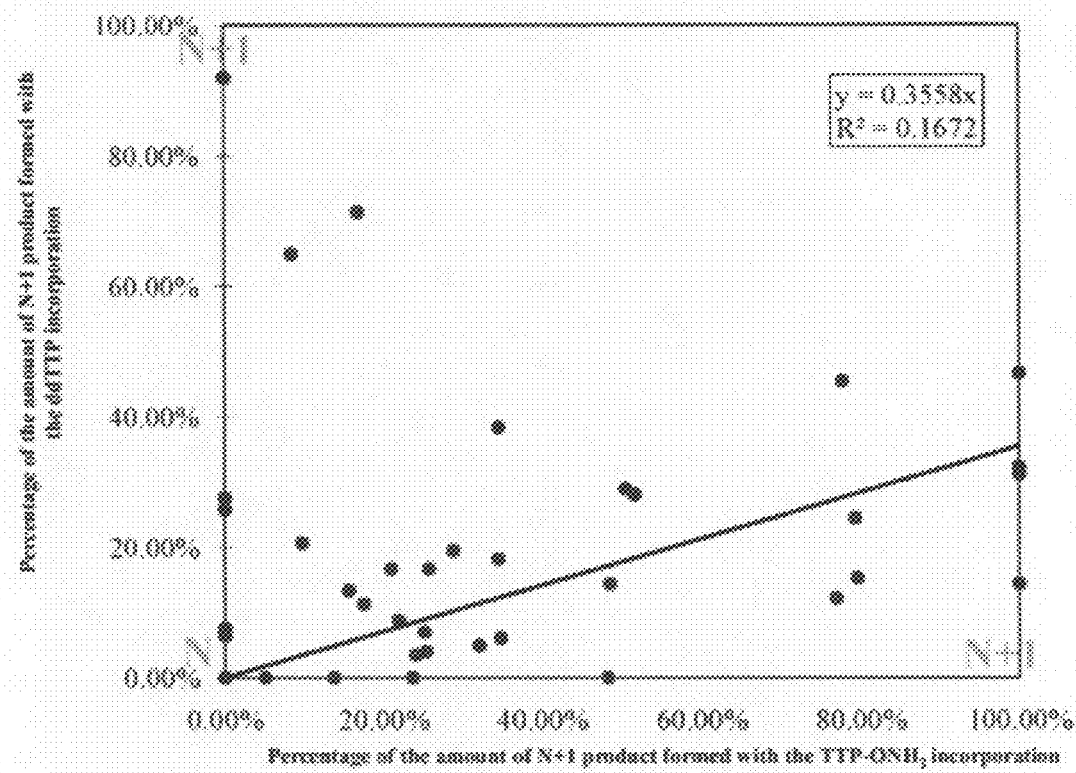
FIG. 10 (A). Example 6. Correlation between the ability of various Taq polymerase variants of PD library to accept reversibly and irreversibly blocked thymidine triphosphates.
Figure 10:
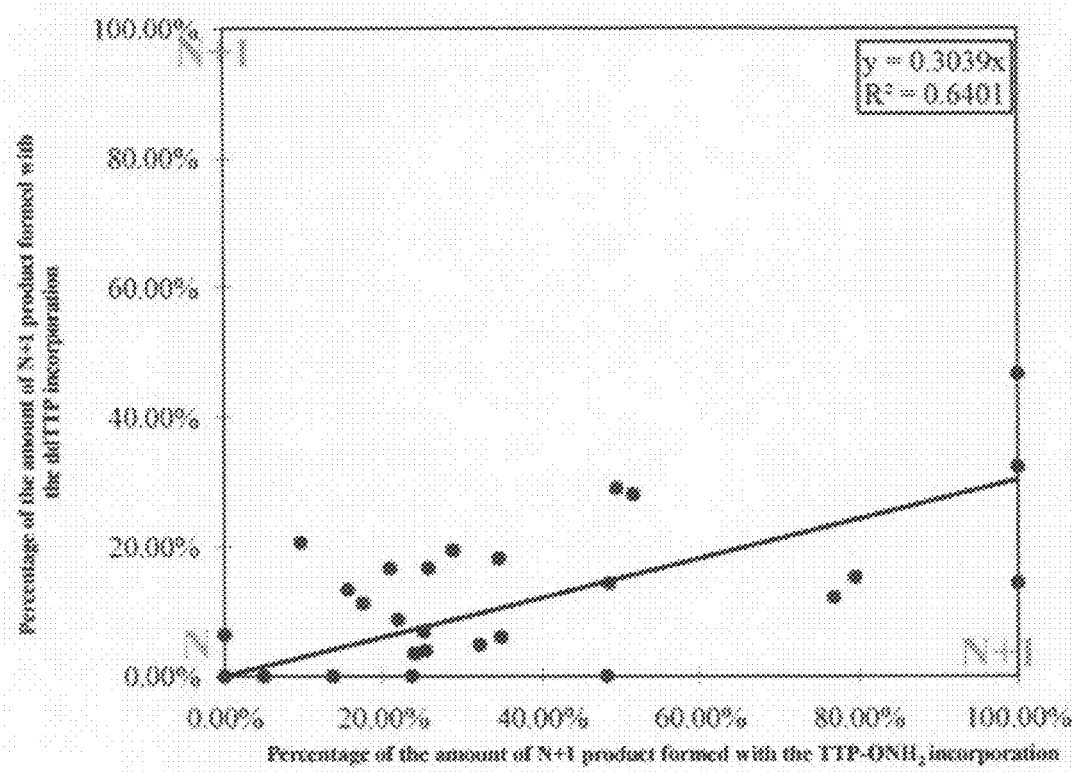

The ability of polymerase variants to accept the 3'-ONH$_2$ reversible terminator in the phylogenetically designed library correlates weakly (r$^2$≈0.167) with the ability of polymerase variants to accept the 2',3'-dideoxynucleoside triphosphate (FIG. 10A). Interestingly, there is a much stronger correlation (r$^2$≈0.64) if variants having a Tyr for Phe replacement at site 667 were removed from the analysis (FIG. 10B). Site 667 was identified a decade ago by Tabor and Richardson, who suggested that the introduction of a hydroxyl group by the replacement of Phe at this site by Tyr was likely to compensate for the loss of the hydroxyl group by the replacement of a 2'-deoxyribonucleoside triphosphate by a 2',3'-dideoxyribonucleoside triphosphate substrate. Thus, this particular change was expected to be directly specific for the dideoxy irreversibly terminating triphosphate. Consistent with this view, the points having a F667Y replacement lie in FIG. 10A above the trend line in the plot of variants lacking this replacement.

TABLE 1

Phylogenetically Designed (PD) Mutant library:

| Culture Number | Mutations Present in PD Taq Library |
|---|---|
| Co-wt-Taq | NONE—wt codon-optimized taq |
| PD-1 | Q489H,K540I,M673G |
| PD-2 | D578F,L609C,A743S |
| PD-3 | T514V,R588V,I614E |
| PD-4 | E520I,V586K,A600S |
| PD-5 | D578F,V586K,M673A |
| PD-6 | F598W,L609P,D625S |
| PD-7 | S513I,A608K,L609S |
| PD-8 | 5576E,D625L,E745H |
| PD-9 | S576E,Y671F,A743S |

TABLE 1-continued

Phylogenetically Designed (PD) Mutant library:

| Culture Number | Mutations Present in PD Taq Library |
|---|---|
| PD-10 | A608G,L616A,E742P |
| PD-11 | N483R,F598V,E745H |
| PD-12 | E520I,D610W,D625S |
| PD-13 | A597C,F667Y,A777H |
| PD-14 | S576E,D578F,F598V |
| PD-15 | N483R,T514V,Y545E |
| PD-16 | A597C,F667H,M673G |
| PD-17 | Q489H,D578T,N583S |
| PD-18 | S513I,A608E,E615I |
| PD-19 | A597C,E615I,M673A |
| PD-20 | S513I,Q582A,I614Q |
| PD-21 | A597T,L609C,R660D |
| PD-22 | T544A,A608G,L609S |
| PD-23 | K540I,Q582A,E745V |
| PD-24 | A600S,A743R,E745V |
| PD-25 | N583Q,A608E,L616I |
| PD-26 | N583S,F598V,A608G |
| PD-27 | N583S,D625L,A777H |
| PD-28 | R536I,R587V,F667L |
| PD-29 | D578T,N583Q,R587V |
| PD-30 | T514V,R536I,D625A |
| P0-31 | A600S,I614E,Y671F |
| PD-32 | L609R,R660D,E742R |
| PD-33 | S576H,D578T,L616I |
| PD-34 | Y545E,V586K,A608E |
| PD-35 | T544A,D578F,L616A,D625A |
| PD-36 | T514V,A597C,L609S,A743R |
| PD-37 | Q489H,R536I,L609C,L616A |
| PD-38 | Q489H,F598V,D625A,F667Y |
| PD-39 | E520I,S576H,A608G,E615I |
| PD-40 | Y545E,R587V,A608K,E615I |
| PD-41 | D578T,A608E,L609C,D625A |
| PD-42 | A597T,L616A,F667Y,E745H |
| PD-43 | D578F,N583Q,W604G,D625S |
| PD-44 | K540I,L609P,A743S,E745H |
| PD-45 | A600S,W604G,L609S,F667H |
| PD-46 | S513I,E520G,D610W,I614E |
| PD-47 | S513I,V586K,R587V,L609P |
| PD-48 | F598W,F667H,Y671F,E742P |
| PD-49 | L609P,I614E,E742R,R746A |
| PD-50 | T544A,I614Q,L616I,D625L |
| PD-51 | K540I,5576E,N583S,D625S |
| PD-52 | N483S,S576E,D610W,A743R |
| PD-53 | D578T,L616D,E742R,A777H |
| PD-54 | A597C,I614E,F667L,A743S |
| PD-55 | N583S,L616A,A743S,R746A |
| PD-56 | S513I,T514V,L616I,E742R |
| PD-57 | 5576E,R587V,A597C,D625S |
| PD-58 | E520G,K540I,L616A |
| PD-59 | Q489H,E520G,A608K |
| PD-60 | S576H,F667Y,R746A |
| PD-61 | T544A,F667L,R746A |
| PD-62 | Y545E,F598W,L609C |
| PD-63 | T544A,L609P,L616D |
| PD-64 | E520I,F598W,A608E,I614E |
| PD-65 | N483R,R536I,A600S,M673G |
| PD-66 | E615I,D625L,F667L,E742P |
| PD-67 | I614Q,M673G,E742P,E745H |
| PD-68 | A600S,A608G,D625A,F667L |
| PD-69 | D610W,I614Q,R660D,E745V |
| PD-70 | Q582A,R660D,F667Y,A743R |
| PD-71 | R536I,K540I,A608K,L616I |
| PD-72 | T514V,E520G,L609C,F667Y |
| PD-73 | D578T,F667H,E745V,R746A |
| PD-74 | V586K,E615I,L616D,Y671F |
| PD-75 | R536I,I614Q,L616D |
| PD-76 | W604G,A608K,D610W |
| PD-77 | A597T,F598W,W604G |
| PD-78 | E520I,Y545E,N583Q,A777H |
| PD-79 | Q582A,I614G,D625A |
| PD80 | S576H,F667H,E742R |
| PD-81 | E520G,W604G,E742P |
| PD-82 | N583Q,L616D,D625L,M673G |
| PD-83 | D578F,L609S,L616I,Y671F |
| PD-84 | A597T,F598V,L609P,M673A |
| PD-85 | E520G,Q582A,A608G,F667H |
| PD-86 | I614G,R660D,M673A,A777H |
| PD-87 | Q582A,W604G,D625L,E742R |
| PD-88 | S576E,L616D,M673A,E745V |
| PD-89 | Y545E,D625S,Y671F,M673A |
| PD-90 | S576H,V586K,F598V,I614Q |
| PD-91 | A608E,R660D,F667L,M673G |
| PD-92 | T544A,F598W,A608K,I614G |
| PD-93 | N483R,Q489H,I614G,E742P |

*All are derivatives of the co-taq gene and inserted into the pASK-IBA43plusvector. Mutations were designed by using "phylogenetic-based approach", and synthesized by DNA 2.0, Inc.

Example 7

Figure 11:
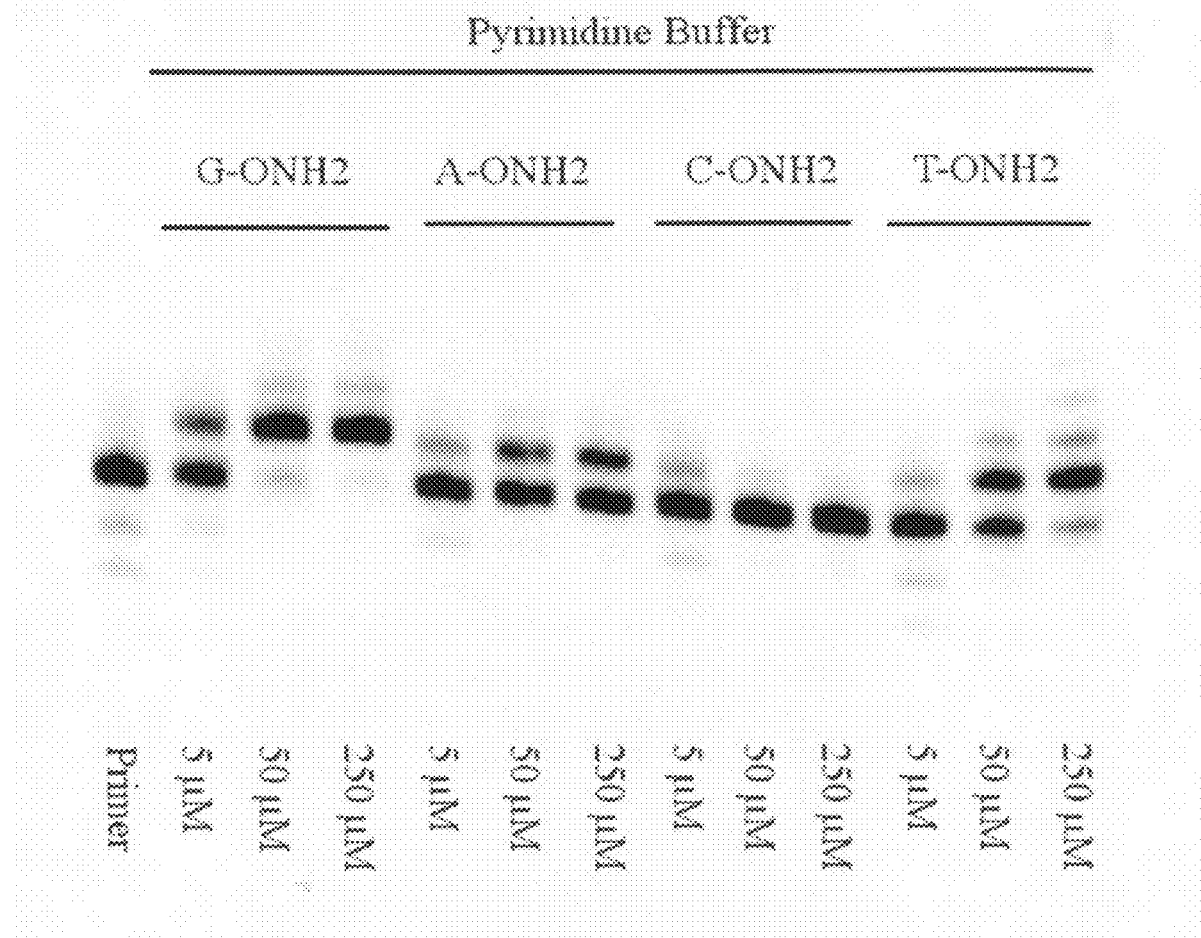
FIG. 11. Example 7. Gel showing tailing of the reversible terminators using terminal transferase.
Figure 12:
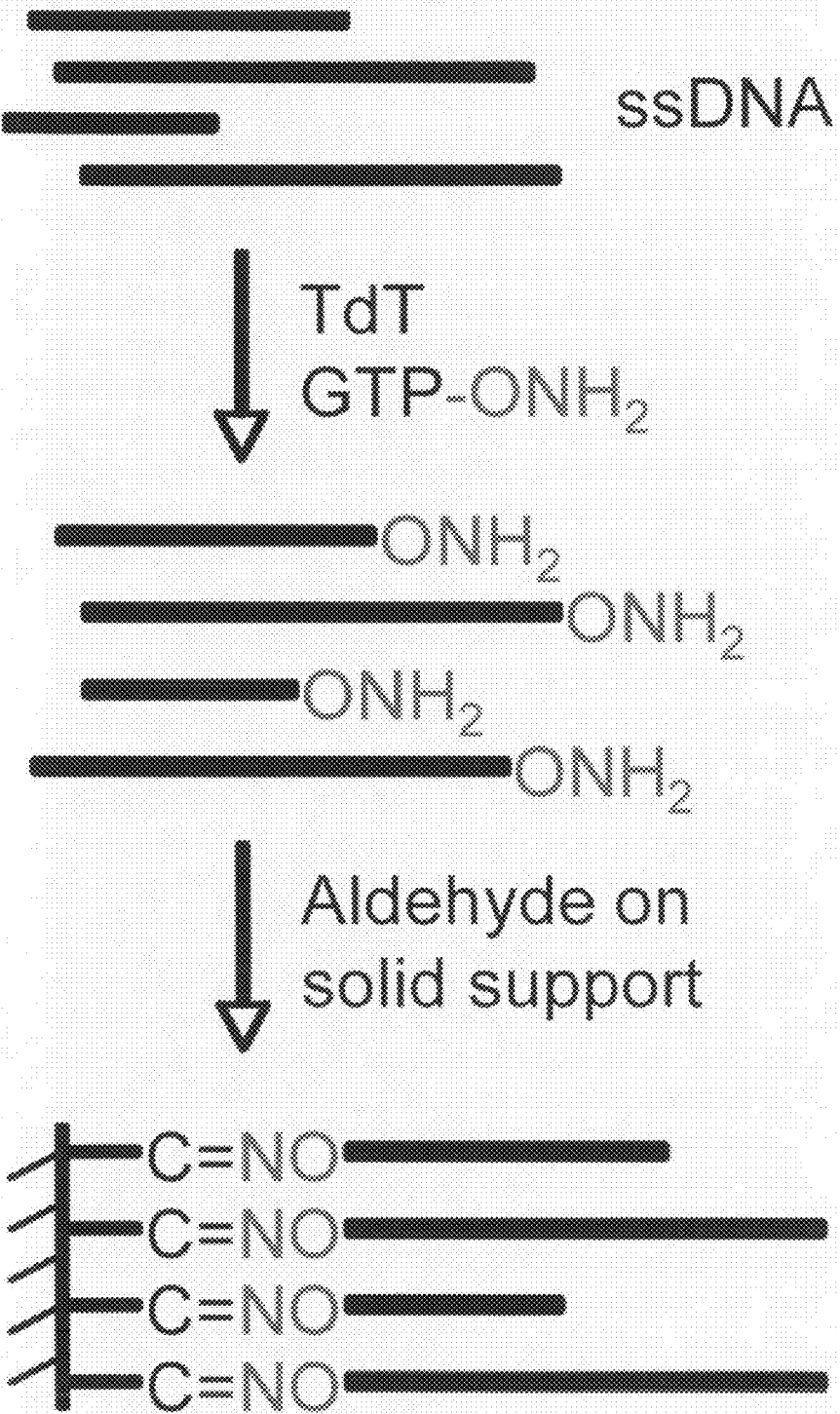
FIG. 12. Example 7. Terminal transferase schematic with capture of the product as oxime FIG. 13. Example 8. Competition between reversible and irreversible terminators.

Appending Nucleotides to an Oligonucleotide Using Terminal Deoxyribonucleotide Transferase (TdT) and Reversible Terminator (FIGS. 11 and 12)

Primers Used
SEQ ID 1 5'-GCGTAATACGACTCACTATGGACG-3'

The oligonucleotide SEQ ID 1 was $^{32}$P-5' labeled using OptiKinase (USB Corporation). Pyrimidine tailing buffer reactions (20 µL) contained 100 mM cacodylate buffer (pH 7.1), 2 mM $CoCl_2$, 0.1 mM DTT, 10 µmol of radiolabeled template (0.5 µM), 10 units of Terminal Transferase (TdT), and varying amounts of reversible terminator from 5 µM to 250 µM. Samples were incubated at 37° C. for 1 hour and were terminated by heating at 70° C. for 10 min. Samples were resolved on 8% PAGE. The results show that tailing of the reversible terminators using TdT seems prefers GTP-$ONH_2$ followed by T, A and C—$ONH_2$. Almost all of the primer was exhausted with GTP-$ONH_2$ and almost all of the primer was remaining when CTP-$ONH_2$ was used as the substrate. FIG. 12 shows a schematic for how the process of the instant invention might be used to capture all single stranded DNA (ssDNA) in a biological mixture. If treated with TdT and a composition of the instant invention, the ssDNA would be derivatized with a 3'-$ONH_2$ group. This could then be captured by an aldehyde affixed to a solid support.

Example 8

Figure 13:
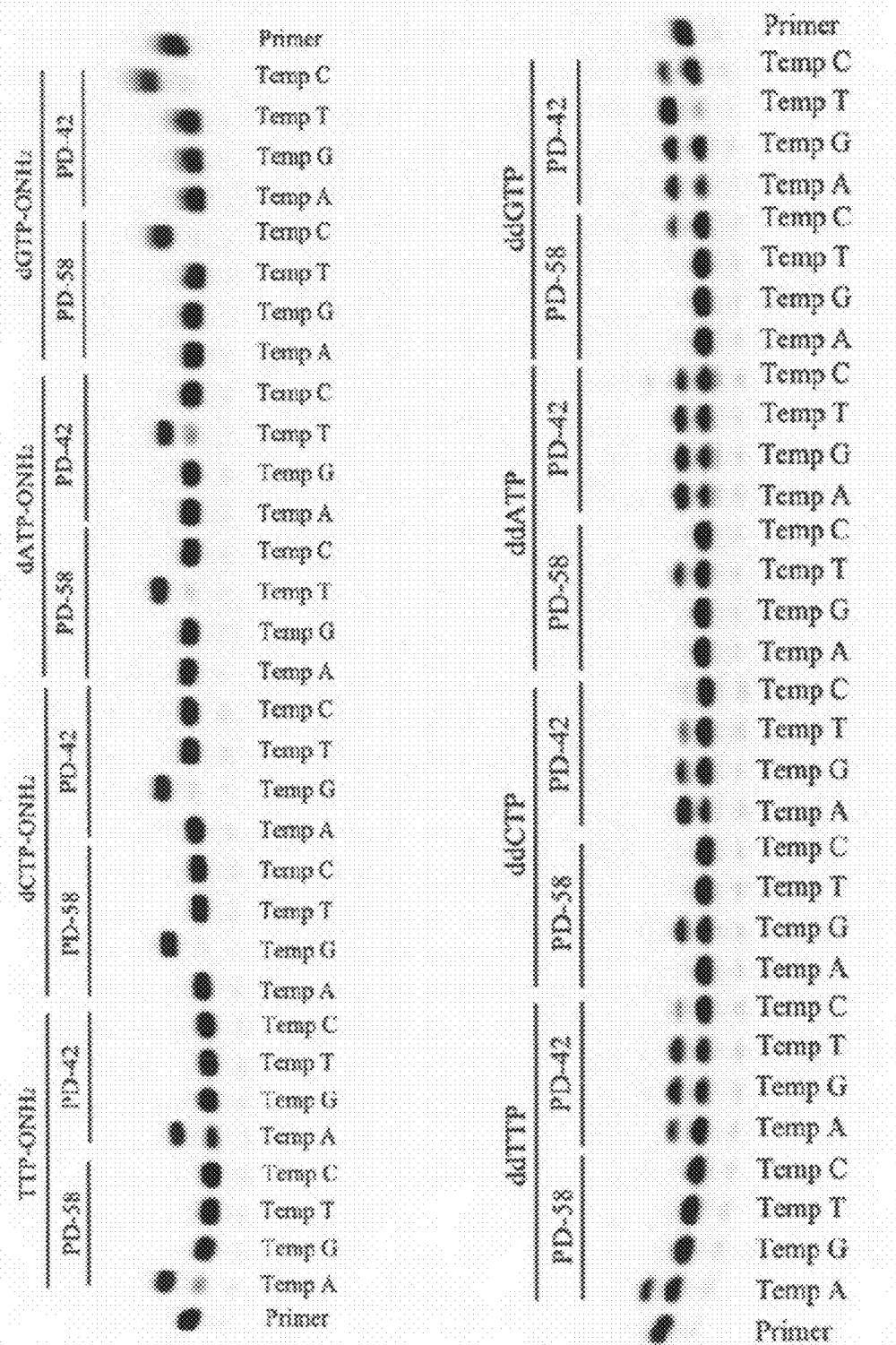

Using Taq Variants PD-42 and PD-58 to Incorporate the Reversible and Irreversible Terminators in Competition (FIG. 13)

Primer and Template:
SEQ ID 1 5'-GCGTAATACGACTCACTATGGACG-3'
SEQ ID 3 3'-CGCATTATGCTGAGTGATACCTGCAAT-GTGCTTCTG-5'
SEQ ID 4 3'-CGCATTATGCTGAGTGATACCTGCGGT-GTGCTTCTG-5'
SEQ ID 5 3'-CGCATTATGCTGAGTGATACCT-GCTTTGTGCTTCTG-5'
SEQ ID 6 3'-CGCATTATGCTGAGTGATACCTGCCCT-GTGCTTCTG-5'
Extension Conditions
In a 10 µL reaction volume, $\gamma^{32}$P-labeled primer SEQ ID 1 (2.5 µmol), cold primer SEQ ID 1 (22.5 µmol) and four kinds of 36 nt long template (30 µmol) (see above) were annealed respectively by incubation at 95° C. for 5 min and slow cooled to room temperature. 1 (0.25 µg/µL) of PD-42 and 58 (polymerases were purified by Qiagen Ni-NTA Spin Kit) were then added to reactions and incubated at 72° C. for 2 min. Reactions were initiated by the addition of dNTP-ONH$_2$ or ddNTP (Final concentration of 100 µM) (refer to FIG. 13 for specifics) and were resolved on a 14% PAGE.

Test the Fidelity for PD-42 and PD-58 to Incorporate the Reversible and Irreversible Terminators Two of the 93 variants that performed well with both dTTP-3'-ONH$_2$ and ddTTP were further examined: PD-42 (A597T, L616A, F667Y, E745H) and PD-58 (E520G, K540I, L616A). The first had the Tabor-Richardson replacement at position 667; the second did not. The fidelities of these were tested using a template that called for a different triphosphate (shown in FIG. 13).

Very little infidelity was observed with both variant PD-42 and PD-58 (FIG. 13, left panel) when challenged to misincorporate reversibly terminated triphosphates. This was evident by the near or complete absence of all misincorporation products. At most, trace amounts of products were seen on by PAGE to indicate a mismatch of incoming dCTP-ONH$_2$ opposite template dC and between incoming dATP-ONH$_2$ opposite template A (SEQ ID 3) using PD-42.

Interestingly, while the fidelity of PD-58 and PD-42 with the reversible terminator appeared to be similarly high, this was not the case when using 2',3'-dideoxy irreversibly terminating triphosphates (FIG. 13, right panel). Here, the PD-58 variant again displayed high fidelity. In contrast (and surprisingly, considering that this contains the P667Y replacement), PD-42 seemed to have lower fidelity with dideoxynucleotides triphosphate. Mismatches happened in almost every mismatch extension reaction.

Example 9

Figure 14:
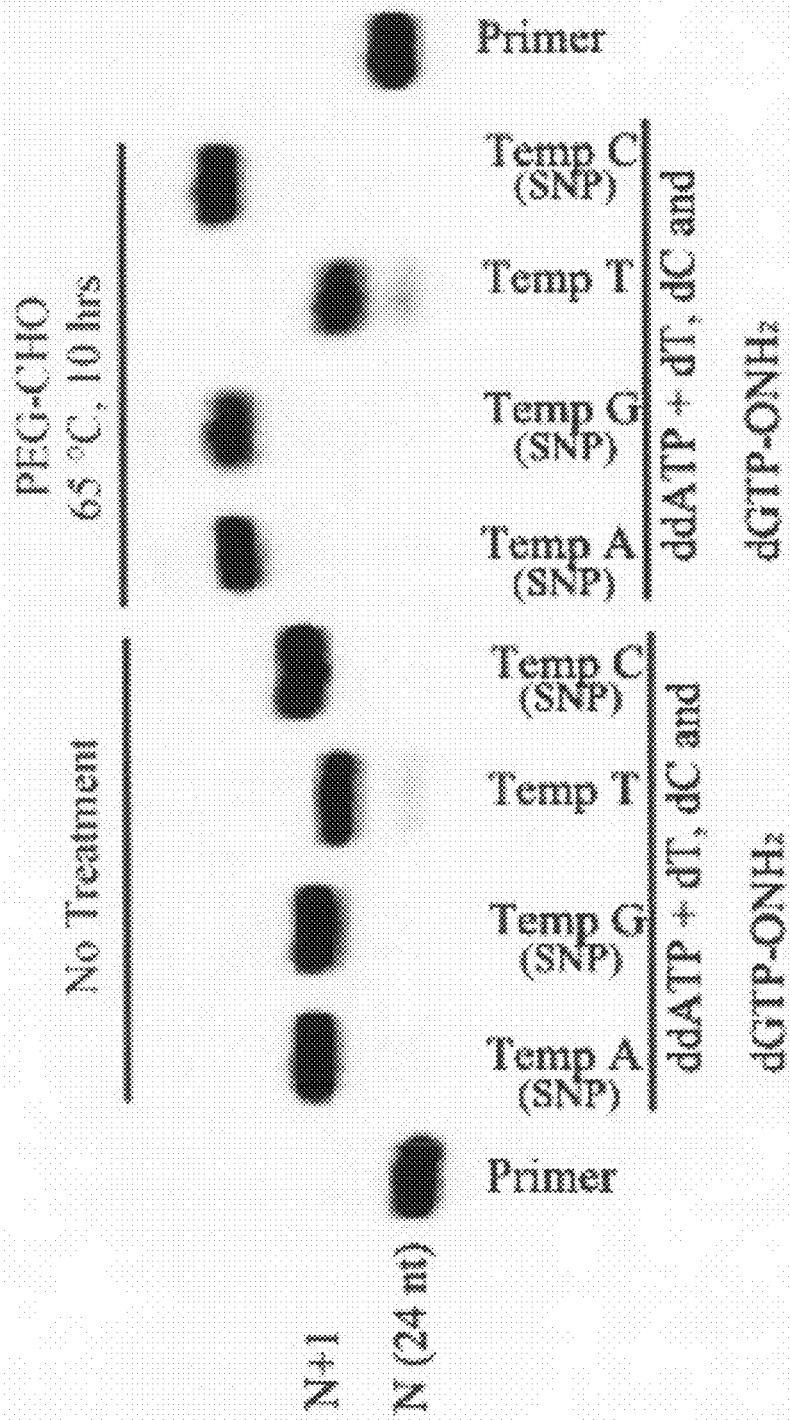
FIG. 14. Example 9. Gel shift showing the PEG-aldehyde capture of 3'-$ONH_2$ reversible terminator extended on SNP template.

SNP Detection Using Capture of an Aldehyde on the 3'-Reversibly Terminated Oligonucleotide (FIG. 14)

Primer and Template:
SEQ ID 1 5'-GCGTAATACGACTCACTATGGACG-3'
SEQ ID 3 3'-CGCATTATGCTGAGTGATACCTGCAAT-GTGCTTCTG-5'
SEQ ID 7 3'-CGCATTATGCTGAGTGATACCTGCGAT-GTGCTTCTG-5'
SEQ ID 8 3'-CGCATTATGCTGAGTGATACCTGCTAT-GTGCTTCTG-5'
SEQ ID 9 3'-CGCATTATGCTGAGTGATACCTGCCAT-GTGCTTCTG-5'

Reaction Conditions

To assess the ability of a combination of reversibly and irreversibly terminating nucleosides to perform together in an architecture designed to detect single-nucleotide polymorphisms, 5'-$^{32}$P-labeled primer SEQ ID 1 (2.5 pmol), cold primer SEQ ID 1 (20 pmol) and template SEQ ID 3, 7, 8, or 9 (30 pmol) were annealed and incubated in 1×NEB ThermoPol Reaction Buffer at 72° C. for 5 min with ddATP (the irreversible terminator), TTP-ONH$_2$, dCTP-ONH$_2$ and dGTP-ONH$_2$ (the reversible terminator) (1 nmol each, 10 µL reaction volume). Primer extension was initiated by adding PD-58 (1 µL of a 0.25 µg/µL solution). Reactions were quenched with 10 mM EDTA (5 µL).

The samples were then treated with 300 mole equivalents of PEG aldehyde (HO—CH$_2$—[CH$_2$—O—CH$_2$]$_2$—CH$_2$—CHO) and incubated at 65° C. overnight. Samples were resolved on a 14% denaturing PAGE and analyzed with a Molecular Imager FX system.

A model experiment (FIG. 14) was done with templates that challenged the PD-58 polymerase variant to incorporate ddATP, TTP-ONH$_2$, dCTP-ONH$_2$ and dGTP-ONH$_2$ at position N+1 opposite template T, A, G, or C (SEQ ID 3, 7, 8, or 9, respectively). The standard template has a T in it, and therefore calls for incorporation of ddATP. This experiment created irreversible products and caused the primer to be irreversibly blocked by incorporating ddATP. Three kinds of SNPs, the T to dA, dG or dC mutations, lead to reversible termination, which may be cleaved, extended and recovered again.

As expected, FIG. 14 showed that the standard template and SNP template calls for incorporation of irreversible and reversible terminator, respectively. Obviously, the primers that were extended with the reversible terminators ran slower than the primers that were extended with the irreversible terminators, and this is further enlarged after PEG aldehyde treatment. There is an obvious shift in the migration of DNA containing —ONH$_2$ after treatment with PEG aldehyde, but the primers that were extended with the nonreversible terminators were not shifted after treatment. This shows that the reversible terminator may be used in SNP detection assays.

What is claimed is:

1. A process comprising (i) incubating a mixture of an oligonucleotide, a terminal deoxyribonucleotide transferase in aqueous solution and one or more 2'-deoxynucleoside triphosphate analogs having the structure

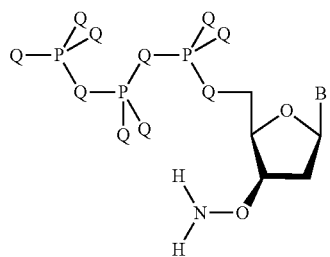

wherein Q is independently selected from the group consisting of O and S, but with not more than one Q being S, and B is a heterocycle selected from the group consisting of adenine, guanine, thymine, cytosine, uracil, diaminopurine, 7-deazaadenine, 7-deazaminoadenine, and 7-deazaguanine, and then (ii) treating the product of said incubation with a reagent that transforms the 3'-ONH$_2$ unit to give a second oligonucleotide product having a 3'-OH unit.

2. The process of claim 1 wherein said process comprises a third step consisting of enzymatic extension of said second oligonucleotide product.

3. The process of claim 1 wherein said reagent is a mixture of nitrous acid and nitrite.

4. The process of claim 3 where the pH is between 5 and 7.

5. A process comprising (i) incubating a mixture of an oligonucleotide primer, an oligonucleotide template, an enzyme selected from the group consisting of DNA polymerase, RNA polymerase, and reverse transcriptase, and one or more 2'-deoxynucleoside triphosphate analogs having the structure

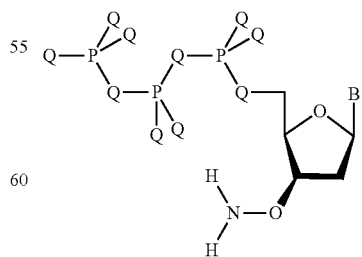

wherein Q is independently selected from the group consisting of O and S, but with not more than one Q being S, and B is a heterocycle selected from the group consisting of adenine, guanine, thymine, cytosine, uracil, diaminopurine, 7-deazaadenine, 7-deazaminoadenine, and 7-deazaguanine, and then (ii) treating the product of said incubation with a reagent that transforms the 3'-ONH$_2$ unit to give a 3'-OH unit.

6. The process of claim 5 wherein said process comprises a third step consisting of enzymatic extension of said second oligonucleotide product.

7. The process of claim 5 wherein said reagent is a mixture of nitrous acid and nitrite.

8. The process of claim 7 where the pH is between 5 and 7.

9. The process of claim 5 wherein said DNA polymerase has an amino acid replacement other than one where a phenylalanine or tyrosine residue in contact with the 2'-deoxyribose ring is replaced by a histidine or a phenylalanine.

10. The process of claim 9 wherein said DNA polymerase is selected from the group consisting of [Taq A597T, L616A, F667Y, E745H], Taq [E520G, K540I, L616A], and Taq [L616A].

11. The process of claim 5 wherein said mixture also includes one or more 2',3'-dideoxyribonucleoside triphosphates.

12. A composition of matter having the structure:

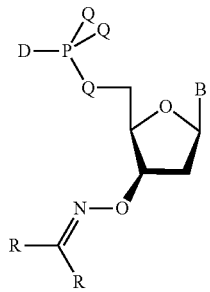

wherein Q is independently selected from the group consisting of O and S, D is a DNA or RNA oligonucleotide, B is a heterocycle selected from the group consisting of adenine, guanine, thymine, cytosine, uracil, diaminopurine, 7-deazaadenine, 7-deazaminoadenine, and 7-deazaguanine, and R is selected from groups consisting of alkyl, alkoxy, and aryl.

13. Compositions of claim 12 wherein one of the R groups is attached to a solid support.

* * * * *